United States Patent
Elmaanaoui

(10) Patent No.: US 11,944,778 B2
(45) Date of Patent: Apr. 2, 2024

(54) METHODS AND SYSTEMS FOR AUTOMATIC PULLBACK TRIGGER

(71) Applicant: Canon U.S.A., Inc., Melville, NY (US)

(72) Inventor: Badr Elmaanaoui, Belmont, MA (US)

(73) Assignee: Canon U.S.A., Inc., Melville, NY (US)

( * ) Notice: Subject to any disclaimer, the term of this patent is extended or adjusted under 35 U.S.C. 154(b) by 77 days.

(21) Appl. No.: 17/381,762

(22) Filed: Jul. 21, 2021

(65) Prior Publication Data
US 2022/0040402 A1    Feb. 10, 2022

Related U.S. Application Data

(60) Provisional application No. 63/133,946, filed on Jan. 5, 2021, provisional application No. 63/062,237, filed on Aug. 6, 2020.

(51) Int. Cl.
*A61B 5/00*    (2006.01)
*A61M 5/00*    (2006.01)
*G06V 10/25*   (2022.01)

(52) U.S. Cl.
CPC ........... *A61M 5/007* (2013.01); *A61B 5/0066* (2013.01); *G06V 10/25* (2022.01)

(58) Field of Classification Search
CPC .......................... A61M 5/007; A61B 5/0066
See application file for complete search history.

(56) References Cited

U.S. PATENT DOCUMENTS

| | | |
|---|---|---|
| 6,763,261 B2 | 7/2004 | Casscells, III et al. |
| 7,366,376 B2 | 4/2008 | Shishkov et al. |
| 7,843,572 B2 | 11/2010 | Tearney et al. |
| 7,872,759 B2 | 1/2011 | Tearney et al. |
| 7,889,348 B2 | 2/2011 | Tearney et al. |
| 8,289,522 B2 | 10/2012 | Tearney et al. |
| 8,412,312 B2 | 4/2013 | Judell et al. |
| 8,676,013 B2 | 3/2014 | Bouma et al. |
| 8,831,321 B1 | 9/2014 | Elbasiony |
| 8,928,889 B2 | 1/2015 | Tearney et al. |

(Continued)

FOREIGN PATENT DOCUMENTS

| | | |
|---|---|---|
| JP | 2013-506136 A | 2/2013 |
| WO | 2010/095370 A1 | 8/2010 |

(Continued)

*Primary Examiner* — Joel F Brutus
(74) *Attorney, Agent, or Firm* — Canon U.S.A., Inc. I.P. Division

(57) ABSTRACT

One or more devices, systems, methods, and storage mediums for optical imaging medical devices, such as, but not limited to, Optical Coherence Tomography (OCT), single mode OCT, and/or multi-modal OCT apparatuses and systems, and methods and storage mediums for use with same, for triggering auto-pullback, including for devices or systems using blood clearing, are provided herein. Examples of applications include imaging, evaluating and diagnosing biological objects, such as, but not limited to, for Gastrointestinal, cardio and/or ophthalmic applications, and being obtained via one or more optical instruments, such as, but not limited to, optical probes, catheters, capsules and needles (e.g., a biopsy needle). Techniques provided herein also improve processing and imaging efficiency while achieving images that are more precise.

14 Claims, 11 Drawing Sheets

(56) References Cited

U.S. PATENT DOCUMENTS

| | | |
|---|---|---|
| 9,076,202 B2 | 7/2015 | Courtney et al. |
| 9,087,368 B2 | 7/2015 | Teamney et al. |
| 9,332,942 B2 | 5/2016 | Jaffer et al. |
| 9,526,424 B2 | 12/2016 | Judell et al. |
| 9,557,154 B2 | 1/2017 | Tearney et al. |
| 9,596,993 B2 | 3/2017 | Kemp et al. |
| 2010/0092389 A1 | 4/2010 | Jaffer |
| 2011/0071405 A1* | 3/2011 | Judell ................ A61B 5/0073 600/479 |
| 2011/0292400 A1 | 12/2011 | Fleming et al. |
| 2012/0101374 A1 | 4/2012 | Teamney et al. |
| 2014/0276011 A1 | 9/2014 | Schmitt et al. |
| 2016/0228097 A1 | 8/2016 | Jaffer et al. |
| 2017/0135584 A1 | 5/2017 | Tearney et al. |
| 2018/0003481 A1 | 1/2018 | Yamada et al. |
| 2018/0045501 A1 | 2/2018 | Elmaanaoui |
| 2019/0298174 A1 | 10/2019 | Watanabe |
| 2019/0374109 A1 | 12/2019 | Wu et al. |
| 2020/0085285 A1 | 3/2020 | Yamada |
| 2021/0077037 A1 | 3/2021 | Kunio |
| 2021/0121132 A1 | 4/2021 | Watanabe et al. |
| 2021/0174125 A1 | 6/2021 | Zhang |

FOREIGN PATENT DOCUMENTS

| | | |
|---|---|---|
| WO | 2016/015052 A1 | 1/2016 |
| WO | 2016/144878 A1 | 9/2016 |
| WO | 2019/046155 A1 | 3/2019 |

\* cited by examiner

METHODS AND SYSTEMS FOR AUTOMATIC PULLBACK TRIGGER

CROSS-REFERENCE TO RELATED APPLICATION(S)

This application relates, and claims priority, to U.S. Patent Application Ser. No. 63/062,237, filed Aug. 6, 2020, and to U.S. Patent Application Ser. No. 63/133,946, filed Jan. 5, 2021, the entire disclosures of which applications are incorporated by reference herein in their entireties.

FIELD OF THE INVENTION

This present disclosure generally relates to computer imaging and/or to the field of optical imaging, particularly to devices, systems, methods, and storage mediums for using multiple imaging modalities, such as, but not limited to, Optical Coherence Tomography (OCT), Multi-mode OCT (MMO-OCT), near-infrared fluorescence (NIRF), near-infrared auto-fluorescence (NIRAF), etc. Examples of OCT applications include imaging, evaluating and diagnosing biological objects, such as, but not limited to, for gastrointestinal, cardio and/or ophthalmic applications, and being obtained via one or more optical instruments, such as, but not limited to, one or more optical probes, one or more catheters, one or more endoscopes, one or more capsules, and one or more needles (e.g., a biopsy needle). One or more devices, systems, methods and storage mediums for characterizing, examining and/or diagnosing, and/or measuring viscosity of, a sample or object in application(s) using an apparatus or system that uses and/or controls multiple imaging modalities are discussed herein.

BACKGROUND OF THE INVENTION

Intravascular imaging (IVI) modalities such as intravascular ultrasound (IVUS) and optical coherence tomography (OCT) provide cross-sectional imaging of coronary arteries with precise lesion information, (e.g., lumen size, plaque morphology, and implanted devices). Additionally, the acquisition rates of these modalities has been increasing like in the case of IVUS with the introduction of high definition (HD) IVUS and other faster high frequency IVUS systems, as well as ever-faster single or multi-modality OCT systems. With these fast systems, automatic pullback mechanisms become even more important where the start of pullback can be algorithmically triggered.

Optical coherence tomography (OCT) is a technique for obtaining high resolution cross-sectional images of tissues or materials, and enables real time visualization. The aim of the OCT techniques is to measure the time delay of light by using an interference optical system or interferometry, such as via Fourier Transform or Michelson interferometers. A light from a light source delivers and splits into a reference arm and a sample (or measurement) arm with a splitter (e.g., a beamsplitter). A reference beam is reflected from a reference mirror (partially reflecting or other reflecting element) in the reference arm while a sample beam is reflected or scattered from a sample in the sample arm. Both beams combine (or are recombined) at the splitter and generate interference patterns. The output of the interferometer is detected with one or more detectors, such as, but not limited to, photodiodes or multi-array cameras, in one or more devices, such as, but not limited to, a spectrometer (e.g., a Fourier Transform infrared spectrometer). The interference patterns are generated when the path length of the sample arm matches that of the reference arm to within the coherence length of the light source. By evaluating the output beam, a spectrum of an input radiation may be derived as a function of frequency. The frequency of the interference patterns corresponds to the distance between the sample arm and the reference arm. The higher frequencies are, the more the path length differences are.

OCT makes use of light for imaging whereas IVUS makes use of sound waves. Acoustic waves can propagate through blood easily except in the case of high frequency ultrasound and HD IVUS where the imaging of the arteries can be degraded with the presence of blood in the lumen. OCT on the other hand may be hindered by the presence of blood in the lumen. As such, for adequate imaging, blood is displaced for a duration of time sufficient for clear imaging. The blood can be displaced using several flushing media like radiopaque contrast agents, saline, Dextran, other blood substitutes, or a combination of media. From rheology it is usually confirmed that radiopaque contrast agents are best at displacing blood in the vessels for clear IVI imaging, OCT for example, and for angiographic imaging. However, care has to be taken to reduce contrast burden since excessive contrast use can lead to nephropathy.

In order to reduce contrast load, flushing has to be done accurately such that the pullback starts at the onset of blood clearing and end right at the end of the blood clearing. Contrast dosage is usually predetermined, for example an imaging run can make use of 10 CC of contrast administered at a rate of 4 CC/sec. When pullback is well timed with contrast administration one can successfully obtain pullback data clear of blood for a full 2 seconds which, for example, can allow for successful imaging of a 50 mm vessel segment at 25 mm/sec pullback rate, or of an 80 mm vessel segment at 40 mm/sec pullback rate.

Manual triggering methods can rely on user reaction time where contrast is administered and the user awaits to see that the image is cleared then triggers the pullback. This method relies on the user's reaction time which can vary from person to person and even for the same person and can be somewhat sluggish such that it might take few hundreds of milliseconds for the user to register that the vessel has cleared then several hundreds more milliseconds before reacting and triggering the start of pullback through an event like a button press, voice command, gesture or other means. A large delay in starting the pullback can lead to blood swirling back into the imaging plane before the whole targeted vessel segment is imaged leading to potentially repeated pullbacks and hence increased contrast administration. Alternatively, the user may elect to administer more contrast per imaging run through using for example a fully filled 20 CC syringe instead of a partially filled syringe or a fully filled smaller 10 CC syringe.

Methods have tried reduce the risk of administering unnecessary contrast through the automatic detection of blood clearance through determination of a line radius for each rotation angle of the probe within a frame and using such information to then trigger the pullback. Such methods require performing several steps like finding a pseudo-radius, then smoothing the radius curve, then finding the largest line radius and since finding a large radius is not sufficient to determine if this corresponds to a clear vessel wall the method is forced to look at a second quality metric to determine if that line radius corresponds to tissue or could be blood measurement. The method also requires few consecutive frames meeting the criteria to trigger rendering it slow to respond at start pullback.

Automatic pullback triggering methods involve a number of parameters which should be modified by the user to adjust the behavior of the flush clearing state, and can be slow to process which may lead to significant delay between onset of vessel clearing and start of pullback. As such, such methods can be unreliable at detecting flushing leading to repeated administration of contrast.

As such, there is a need for a method that automatically triggers a pullback. Indeed, there is a need to provide reliable, efficient measurements for the whole OCT pullback.

Accordingly, it would be desirable to provide at least one imaging or optical device, system, method, and storage medium for using, controlling, and/or emphasizing one or more multiple imaging modalities, for example, by using a method or methods that trigger an automatic pullback, and/or that provide reliable and efficient measurements and imaging for the whole OCT pullback.

SUMMARY OF THE INVENTION

Accordingly, it is a broad object of the present disclosure to provide imaging (e.g., OCT, NIRF, NIRAF, etc.) apparatuses, systems, methods and storage mediums for using and/or controlling an auto-pullback triggering method in one or more apparatuses or systems (e.g., an intracoronary imaging apparatus or system). It is also a broad object of the present disclosure to provide OCT devices, systems, methods and storage mediums using an interference optical system, such as an interferometer (e.g., SD-OCT, SS-OCT, MM-OCT, etc.).

One or more embodiments of the present disclosure avoid the aforementioned issues by providing a simple and fast method or methods that uses/use a smaller subset of the image frame data and is using simple subtraction of the consequent frames data from a reference frame therefore looking for a metric that represents the change in data and is therefore less prone to noise from non-blood features hence is more sensitive to change in the state of the lumen from blood filled to clear. The method(s) then relies/rely on a simple change in intensity as the metric and is very robust and fast that it is significantly real time.

In one or more embodiments, at least one method may automatically trigger the pullback (e.g., without any user interaction, does not require user interaction, etc.). As such, in one or more embodiments a whole targeted object, sample, or area (e.g., a vessel) may be imaged minimizing the contrast overdosing risk (e.g., radiographic contrast overdose is reduced, avoided, or minimized by limiting, minimizing, or avoiding the use of a contrast agent).

One or more embodiments of the present disclosure may involve a method for triggering an automatic pullback during imaging (e.g., intravascular imaging).

One or more embodiments of the present disclosure relate generally to the field of imaging that requires triggering of pullbacks upon clearance of blood from vessel lumens. Examples of such applications include imaging, evaluation and diagnosis of biological objects, such as, but not limited to, intravascular applications, being obtained via one or more instruments, such as, but not limited to, one or more probes, one or more catheters and one or more tethered capsules.

Intraluminal imaging aims to acquire high-resolution cross-sectional images of tissue and enable real time visualization. Intraluminal imaging may clear blood from lumen to image blood vessel segments in one or more embodiments. Pullbacks may be triggered manually or algorithmically. Manual triggering of the pullbacks may lead to a large delay in starting the pullback.

One or more embodiments of the present disclosure overcome the aforementioned issues since one or more embodiments of the present disclosure ensure that pullback may reliably start at the onset of blood vessel clearing, minimizing the time and volume of contrast that needs to be administered per imaging run and ensuring that imaging is not missed for good vessel clearing runs, without need for complex parameters and lengthy complex processing.

In one or more embodiments of the present disclosure, an imaging device for triggering a (manual or automatic) pullback may include: one or more processors that operate to: collect image data from a blood vessel lumen; determine a change in an image intensity relative to a reference frame region of interest (ROI); and issue a signal based on an amount of, or a level in, the change, the signal operating to trigger the automatic pullback.

In one or more embodiments, the one or more processors may further operate to one or more of the following: (i) acquire a next frame of the ROI; (ii) isolate the ROI such that in a pre-scan conversion domain the data is selected such that a band of two-dimensional (2D) images start a few pixels outside an outer radius of a catheter and extend for a depth equivalent to about a penetration depth in blood; (iii) receive one or more imaging modality frames at a rate of up to 200 frames per second; (iv) select the ROI from about 90 pixels in depth to 160 pixels in depth and for either all A-lines or from A-line 1 to A-line 500; (v) capture the reference frame in a low rotation speed mode and adjust the reference frame to match the ROI for frames used to detect the automatic pullback trigger; (vi) capture the reference frame in a low rotation speed mode and adjust the reference frame to match the ROI for frames used to detect the automatic pullback trigger, and use the reference frame as the reference ROI, instead of acquiring the next frame ROI, in a situation where values from the reference frame are indicative of a possible preclearing image; and/or (vii) determine whether the possible preclearing image includes a case where contrast is or was administered by mistake sooner or earlier than the imaging device was put in a pre-record mode and/or a pullback mode.

In one or more embodiments, the one or more processors may further operate to one or more of the following: (i) process or display the ROI as an annulus on a scan converted image of a partly cleared vessel image with overlaid annulus inner and outer rings; (ii) process or display the ROI with a blacked out background for the image beyond the annulus; (iii) perform subsampling in the A-lines direction to improve or optimize processing; and/or (iv) process the subsampling every other A-line or one A-line for every three or more A-lines.

In one or more embodiments, the one or more processors may further operate to one or more of the following: (i) acquire a next frame of the ROI, or use the reference frame as the reference ROI in a situation where values from the reference frame are indicative of a possible preclearing image; (ii) identify a first frame of the ROI; (iii) store the first frame as an original image of the ROI; (iv) store the first frame as an original image of the ROI in a memory; (v) compute or determine a clearance metric; (vi) determine whether the clearance metric is above a threshold; (vii) in the event that the clearance metric is not above the threshold, then return to acquire a next frame of the ROI, identify a new first frame, and compute or determine a new clearance metric until the clearance metric is above the threshold;

and/or (viii) in the event that the clearance metric is above the threshold, trigger the automatic pullback.

In one or more embodiments, the one or more processors may further operate to one or more of the following: (i) subtract every subsequent frame ROI data from the reference ROI; (ii) subtract every subsequent frame ROI data from the reference ROI such that substantially similar features or the same features are substantially subtracted or are subtracted from each other; (iii) calculate or determine the clearance metric to be one or more of the following: a sum or mean value for 8-bit unsigned integer values in the ROI of all subsequent frames, a sum or mean value for 8-bit unsigned integer intensity values in the ROI of all subsequent frames subtracted from the reference ROI, a sum or mean value for 8-bit unsigned integer intensity values in the ROI of all subsequent frames subtracted from the reference ROI then divided by the mean of the current frame ROI, a sum or mean value for 8-bit unsigned integer intensity values in the ROI of all subsequent frames subtracted from the reference ROI then divided by the mean of the reference ROI, a mean ROI value of the resultant signal, a mean ROI value of the resultant signal relative to the mean ROI value from the reference frame ROI, a mean ROI value of the resultant signal relative to the mean ROI value from the current frame ROI value, a region with a large or the highest change, and/or one or more regions to be compared with one or more thresholds; and/or (iv) perform pre-blood clearance and/or post-blood clearance such that the pre-blood clearance and/or post-blood clearance is a minimal part of a whole change leading to smaller changes in the clearance metric.

In one or more embodiments, one or more of the following may occur or exist: (i) the ROI original frames are acquired for several frames including one or more of the following: blood filled lumen, partially clear lumen, and/or diagnostically clear vessel wall(s); (ii) the threshold is a pre-determined or set threshold value; (iii) the clearance metric is computed for n segments of the ROI, where n is one or more of the following: an integer value from 2 and up to half the number of processed A-lines in the ROI, is in the range of 2 to 4, and/or is in the range of 2 to 8; (iv) the threshold is set so that the automatic pullback is triggered after partial clearing or only after diagnostic clearing is achieved; (v) the threshold is set to optimize the automatic pullback such that time taken from issuance of the trigger pullback to an actual motion of a pullback mechanism is in a tens of milliseconds range; and/or (vi) the threshold is set to a high value such that the clearance metric only exceeds the threshold for an image that is equivalent or substantially equivalent to a diagnostically clear image, or the threshold is set low for a situation where a delay between the issuance of the trigger pullback to the actual motion of the pullback mechanism is larger than 100 milliseconds such that the clearance metric exceeds the low threshold for an image that is equivalent or substantially equivalent to a partly or partially clear image.

In one or more embodiments, the one or more processors may further operate to one or more of the following: (i) use digitizers or modern digitizers that have one or more built-in Field Programmable Gate Arrays ("FPGAs") for controlling data flow that are capable of OCT processing; (ii) perform the OCT processing including one or more of the following: windowing of data, zero-padding, Fast Fourier Transform (FFT), magnitude calculation, and/or taking a logarithm of a result before issuance of the trigger pullback signal; (iii) after the issuance of the trigger pullback signal, transfer raw data from the digitizer or the modern digitizer and saving and processing the raw data at a lower rate than a rate at which the raw data was acquired; and/or (iv) in a scenario with two detection channels, use a single channel for faster processing of data before issuance of the trigger pullback signal, and, after the issuance of the trigger pullback signal, use both detection channels.

In one or more embodiments, one or more of the following may occur or exist: (i) the clearance metric is kept for more than one frame and a preliminary threshold for a pre-trigger that is indicative of a partial clearing is used; (ii) in a scenario where the trigger pullback threshold is reached, the trigger pullback is started only if the clearance metric has exceeded the pre-trigger threshold for a certain minimum number of frames; (iii) the certain minimum number of frames is one or more; and/or (iv) if not a number of consecutive frames, one or more frames have the clearance metric exceed the trigger pullback threshold before the trigger pullback signal is issued.

In one or more embodiments of a method(s) of the present disclosure, at least one method for triggering a (manual or automatic) pullback may include: collecting image data from a blood vessel lumen; determining a change in an image intensity relative to a reference frame region of interest (ROI); and issuing a signal based on an amount of, or a level in, the change, the signal operating to trigger the automatic pullback.

One or more method embodiments may further include one or more of the following: (i) acquiring a next frame of the ROI; (ii) isolating the ROI such that in a pre-scan conversion domain the data is selected such that a band of two-dimensional (2D) images start a few pixels outside an outer radius of a catheter and extend for a depth equivalent to about a penetration depth in blood; (iii) receiving one or more imaging modality frames at a rate of up to 200 frames per second; (iv) selecting the ROI from about 90 pixels in depth to 160 pixels in depth and for either all A-lines or from A-line 1 to A-line 500; (v) capturing the reference frame in a low rotation speed mode and adjusting the reference frame to match the ROI for frames used to detect the automatic pullback trigger; (vi) capturing the reference frame in a low rotation speed mode and adjusting the reference frame to match the ROI for frames used to detect the automatic pullback trigger, and using the reference frame as the reference ROI, instead of acquiring the next frame ROI, in a situation where values from the reference frame are indicative of a possible preclearing image; and/or (vii) determining whether the possible preclearing image includes a case where contrast is or was administered by mistake sooner or earlier than the imaging device was put in a pre-record mode and/or a pullback mode.

One or more method embodiments may further include one or more of the following: (i) processing or displaying the ROI as an annulus on a scan converted image of a partly cleared vessel image with overlaid annulus inner and outer rings; (ii) processing or displaying the ROI with a blacked out background for the image beyond the annulus; (iii) performing subsampling in the A-lines direction to improve or optimize processing; and/or (iv) processing the subsampling every other A-line or one A-line for every three or more A-lines.

One or more method embodiments may further include one or more of the following: (i) acquiring a next frame of the ROI, or using the reference frame as the reference ROI in a situation where values from the reference frame are indicative of a possible preclearing image; (ii) identifying a first frame of the ROI; (iii) storing the first frame as an original image of the ROI; (iv) storing the first frame as an original image of the ROI in a memory; (v) computing or determining a clearance metric; (vi) determining whether the clearance metric is above a threshold; (vii) in the event that the clearance metric is not above the threshold, then returning to acquire a next frame of the ROI, identify a new first frame, and compute or determine a new clearance metric until the clearance metric is above the threshold; and/or (viii) in the event that the clearance metric is above the threshold, triggering the automatic pullback.

One or more method embodiments may further include one or more of the following: (i) subtracting every subsequent frame ROI data from the reference ROI; (ii) subtracting every subsequent frame ROI data from the reference ROI such that substantially similar features or the same features are substantially subtracted or are subtracted from each other; (iii) calculating or determining the clearance metric to be one or more of the following: a sum or mean value for 8-bit unsigned integer values in the ROI of all subsequent frames, a sum or mean value for 8-bit unsigned integer intensity values in the ROI of all subsequent frames subtracted from the reference ROI, a sum or mean value for 8-bit unsigned integer intensity values in the ROI of all subsequent frames subtracted from the reference ROI then divided by the mean of the current frame ROI, a sum or mean value for 8-bit unsigned integer intensity values in the ROI of all subsequent frames subtracted from the reference ROI then divided by the mean of the reference ROI, a mean ROI value of a resultant signal, a mean ROI value of a resultant signal relative to the mean ROI value from the reference frame ROI, a mean ROI value of a resultant signal relative to the mean ROI value from the current frame ROI value, a region with a large or the highest change, and/or one or more regions to be compared with one or more thresholds; and/or (iv) performing pre-blood clearance and/or post-blood clearance such that the pre-blood clearance and/or post-blood clearance is a minimal part of a whole change leading to smaller changes in the clearance metric.

One or more storage medium embodiments may be provided for storing a computer-readable program for causing a computer to execute a method for triggering an automatic pullback, where the method may include: collecting image data from a blood vessel lumen; determining a change in an image intensity relative to a reference frame region of interest (ROI); and issuing a signal based on an amount of, or a level in, the change, the signal operating to trigger the automatic pullback.

The present disclosure describes a means to allow OCT users to focus on the area of interest and/or to perform auto-pullback triggering in all imaging modalities, such as, but not limited to, a tomography image, near-infrared fluorescence (NIRF) information in carpet view, three-dimensional (3D) rendering of a coronary vessel in a half pipe display, lumen diameter display, longitudinal view, and angiography view. This allows the users to get a full view of the structural vessel information using one modality or multi-modalities and allows configurability of the function for more targeted focus when providing the fast, efficient A-line lumen segmentation method(s).

In accordance with one or more embodiments of the present disclosure, apparatuses and systems, and methods and storage mediums for auto-pullback triggering may operate to characterize biological objects, such as, but not limited to, blood, mucus, tissue, etc.

One or more embodiments of the present disclosure may be used in clinical application(s), such as, but not limited to, intervascular imaging, intravascular imaging, atherosclerotic plaque assessment, cardiac stent evaluation, intracoronary imaging using blood clearing, balloon sinuplasty, sinus stenting, arthroscopy, ophthalmology, ear research, veterinary use and research, etc.

In accordance with at least another aspect of the present disclosure, one or more technique(s) discussed herein may be employed as or along with features to reduce the cost of at least one of manufacture and maintenance of the one or more apparatuses, devices, systems and storage mediums by reducing or minimizing a number of optical and/or processing components and by virtue of the efficient techniques to cut down cost of use/manufacture of such apparatuses, devices, systems and storage mediums.

The following paragraphs describe certain explanatory embodiments. Other embodiments may include alternatives, equivalents, and modifications. Additionally, the explanatory embodiments may include several novel features, and a particular feature may not be essential to some embodiments of the devices, systems, and methods that are described herein.

According to other aspects of the present disclosure, one or more additional devices, one or more systems, one or more methods and one or more storage mediums using OCT and/or other technique(s) are discussed herein. Further features of the present disclosure will in part be understandable and will in part be apparent from the following description and with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein.

DETAILED DESCRIPTION OF THE PRESENT INVENTION

Figure 1:
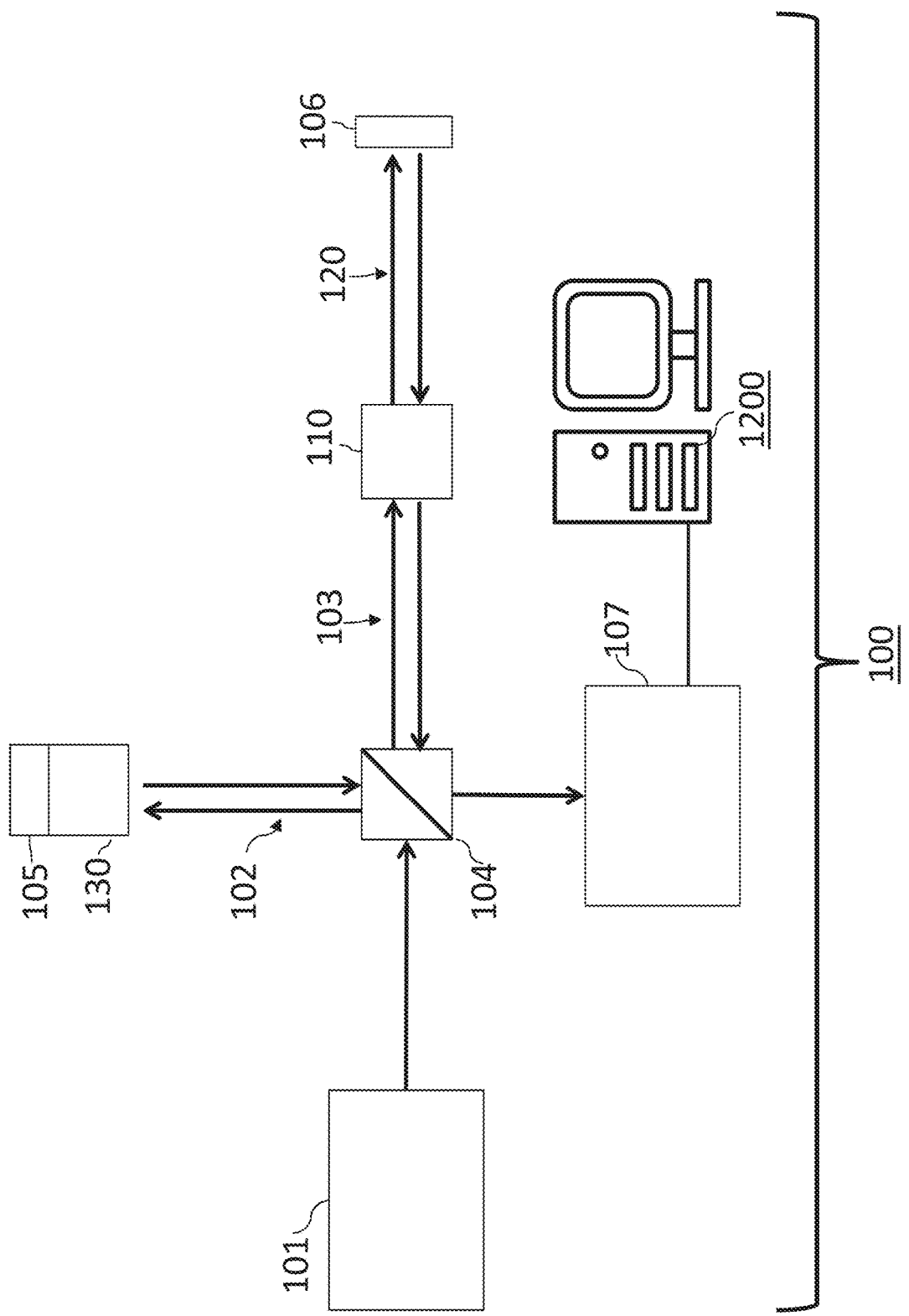
FIG. 1 is a schematic diagram showing at least one embodiment of a system that may be used for performing one or more embodiments of an automatic pullback trigger method(s) in accordance with one or more aspects of the present disclosure.

One or more devices, systems, methods and storage mediums for characterizing tissue, or an object or sample, using one or more imaging and/or calculation techniques or modalities (such as, but not limited to, OCT, NIRF, NIRAF, etc.) are disclosed herein. Several embodiments of the present disclosure, which may be carried out by the one or more embodiments of an apparatus, system, method and/or computer-readable storage medium of the present disclosure are described diagrammatically and visually in FIGS. 1 through 11.

In one or more embodiments, at least one method may detect a clearing state of blood in a target object, sample, or area (e.g., a vessel) and may automatically trigger the pullback (e.g., without any user interaction, does not require user interaction, etc.). As such, in one or more embodiments a whole targeted object, sample, or area (e.g., a vessel) may be imaged minimizing the contrast overdosing risk (e.g., radiographic contrast overdose is reduced, avoided, or minimized).

One or more embodiments of the present disclosure may involve one or more of the following: using an annulus like region of interest (ROI) so as to minimize or reduce data to be used for computation and to avoid catheter/probe and vessel wall contribution; tracking change is/as signal as a metric to substantially subtract signal from structure like vessel wall and guide wire thus increasing signal change between blood filled vessel frame and partially clear or diagnostically clear frames; using sections of ROI to improve or optimize signal change to sections that are in the vessel lumen only and not vessel wall or guide wire; using subtraction and averaging which is extremely fast and may be run on every frame in less time than it takes for a new frame to be acquired; and/or having different threshold value improved or optimized to inherent system delay from decision to start pullback until pullback actually takes effect.

One or more embodiments of the present disclosure may involve a method for triggering an automatic pullback during imaging (e.g., intravascular imaging), and may include the following: collecting imaging data from a blood vessel lumen or other target, determining using a computer a processor a change in image intensity relative to a reference frame region of interest (ROI) and issuing a signal (e.g., to trigger the automatic pullback) based on a level of change. One or more apparatuses or systems discussed herein (or another apparatus or system) may use the one or more method embodiments for triggering pullback.

In one or more embodiments having no user interaction, one or more methods thereof do not require any parameter(s) to be modified by the user to adjust the behavior of the flush clearing state (e.g., when the algorithm or method fails). Indeed, reducing or avoiding user interaction improves efficiency and reduces error(s).

Turning now to the details of the figures, processing intravascular imaging data and/or performing auto-pullback triggering method(s) may be performed in one or more ways as discussed herein. One or more displays discussed herein may allow a user of the one or more displays to use, control and/or emphasize one or more imaging and/or calculation techniques or modalities, such as, but not limited to, OCT, NIRF, NIRAF, etc., and may allow the user to use, control, and/or emphasize the one or more imaging techniques or modalities synchronously, and/or may allow the user to perform auto-pullback triggering method(s) (including method(s) involving blood clearing) and/or to process intravascular imaging data.

Intravascular imaging modalities like OCT use optical signals to image vessel lumen, wall surface and about 1-2 mm within the vessel wall. Because blood strongly attenuates OCT light, a flushing agent may be used to displace blood for a duration of time sufficient for a proper pullback to occur. Usually viscous radiopaque contrast agents may be used instead of saline so as to flush at a reduced rate that is safe for the arterial walls of the vessel (3-4 CC/sec typically). In one or more embodiments, blood clearance may be synchronized with the catheter pullback to ensure that the whole arterial segment is imaged during the limited time the contrast agent is administered (2.5-4.0 seconds). Contrast is administered for a short period of time to limit the amount of contrast since radiopaque contrast can be toxic in large volume and has been shown to cause renal insufficiency and failure in some patients. Adequate synchronization where the time between clearance of the vessel and start of pullback is of the utmost important and is the main requirement for any pullback auto triggering mechanism. If the pullback starts too soon then the distal segment of the vessel will not have diagnostic worthy clear artery wall images. Likewise, if the pullback starts too late then the proximal segment of the vessel will not have diagnostic worthy clear artery wall images.

As shown diagrammatically in FIG. 1, one or more embodiments of a system or apparatus for visualizing, emphasizing and/or controlling one or more imaging modalities, and/or for performing auto-pullback triggering method(s) (including method(s) involving blood clearing) and/or to process intravascular imaging data, of the present disclosure may be involved with one or more predetermined or desired procedures, such as, but not limited to, medical procedure planning and performance.

Figure 2:
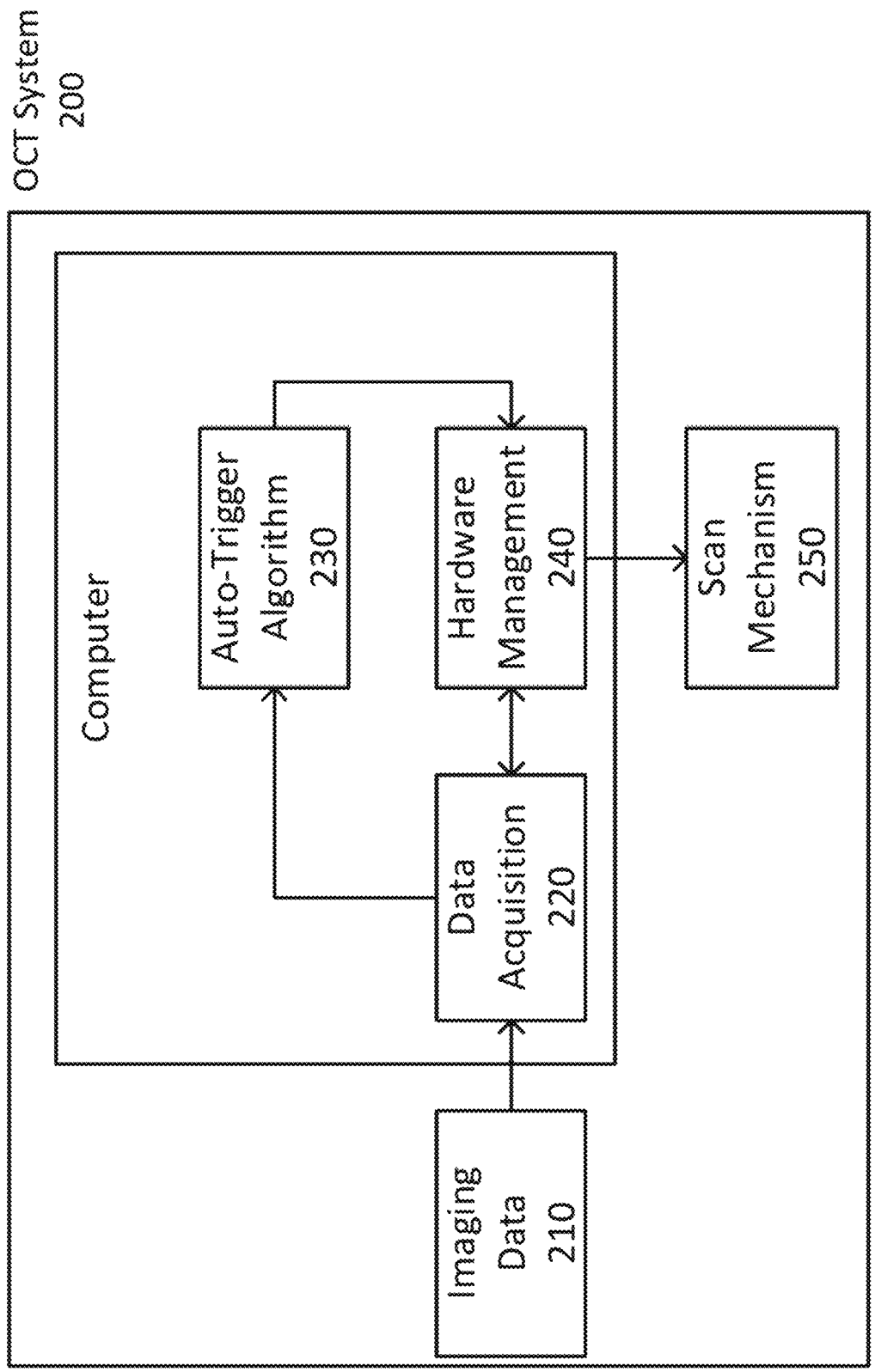
FIG. 2 is a generalized schematic diagram of at least one additional embodiment of a system or apparatus that may be used to performing one or more embodiments of an automatic pullback trigger method(s) in accordance with one or more aspects of the present disclosure.

FIG. 2 shows a generalized schematic diagram of an exemplary embodiment according to the present invention which can include an optical coherence tomography system. The system can also be dual modality, OCT and near infrared auto-fluorescence (NIRAF). The imaging data 210 can be acquired using a data acquisition unit 220. A hardware management unit 240 can control the data acquisition unit 220 parameters and the scan mechanism unit 250. The Auto-Trigger Algorithm unit 230 can, using data from the data acquisition unit 220, initiate a pullback through the hardware management unit 240. This is not limiting for the unit 230 can directly direct unit 220 to get data for recording and to control the unit 250 directly to start the pullback.

There may also be other blocks and units between unit 230 and other units that are not depicted in the diagram.

Electrical analog signals obtained from the output of the system of FIG. 1 are converted to digital signals to be analyzed with a computer, such as, but not limited to, the computer of FIG. 1, the computer of FIG. 2, the computer 1200, 1200' (shown in FIGS. 1 and 7-10 and FIG. 11, respectively, discussed further below), etc. In one or more embodiments, a Fourier analyzer including software and electronics may be used to convert the electrical analog signals into an optical spectrum. In one or more embodiments, the computer of FIG. 2 may be the computer 1200 or the computer 1200'.

Descriptions of like-numbered elements present in the system(s) of FIG. 1 and/or FIG. 2 and already described above shall not be repeated, and are incorporated by reference herein in their entireties.

In accordance with at least one aspect of the present disclosure, a feature of OCT systems is implemented using fiber optics. As aforementioned, one application of an OCT technique of the present disclosure is to use OCT with a catheter 120 as schematically shown in at least FIGS. 1 and 3.

Figure 3:
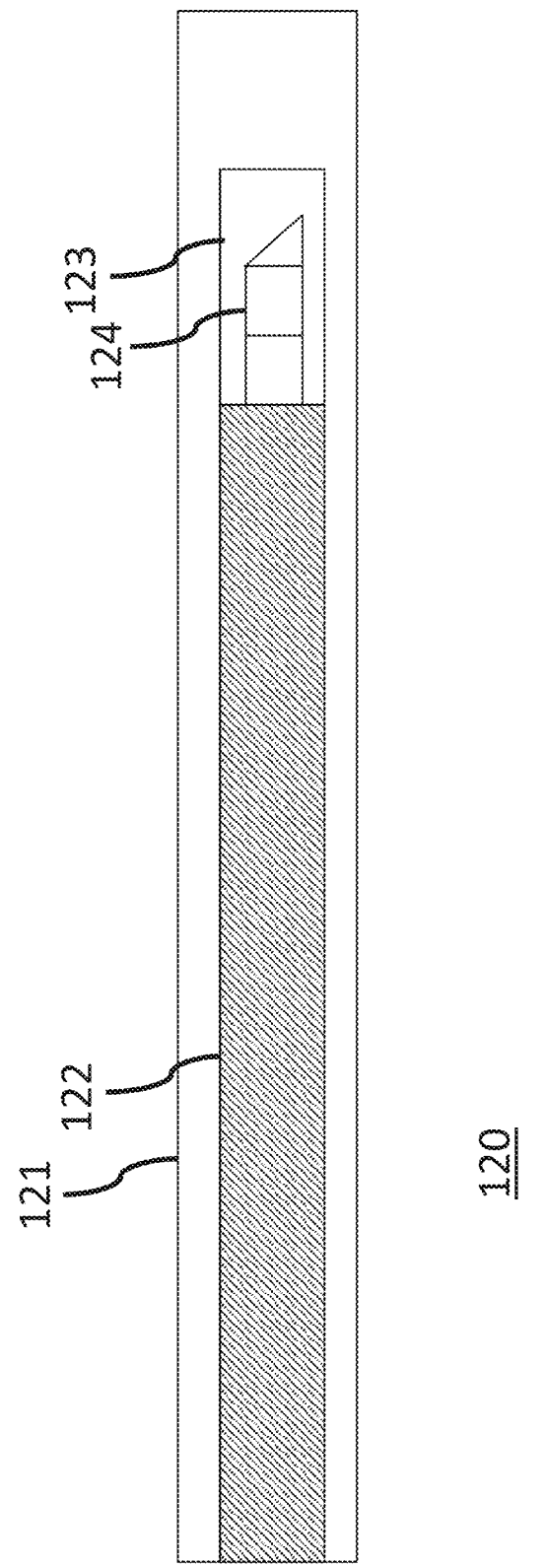
FIG. 3 is a diagram of an embodiment of a catheter or probe that may be used with at least one embodiment of an apparatus, method, or system for performing automatic pullback trigger techniques in accordance with one or more aspects of the present disclosure.

FIG. 3 shows an embodiment of the catheter 120 including a sheath 121, a coil 122, a protector 123 and an optical probe 124. As shown schematically in FIGS. 1 and 3, the catheter 120 preferably is connected to the PIU 110 to spin the coil 122 with pullback (e.g., at least one embodiment of the PIU 110 operates to spin the coil 122 with pullback). The coil 122 delivers torque from a proximal end to a distal end thereof (e.g., via or by a rotational motor in the PIU 110). In one or more embodiments, the coil 122 is fixed with/to the optical probe 124 so that a distal tip of the optical probe 124 also spins to see an omnidirectional view of a biological organ, sample or material being evaluated, such as, but not limited to, hollow organs such as vessels, a heart, etc. For example, fiber optic catheters and endoscopes may reside in the sample arm (such as the sample arm 103 as shown in FIG. 1) of an OCT interferometer in order to provide access to internal organs, such as intravascular images, gastro-intestinal tract or any other narrow area, that are difficult to access. As the beam of light through the optical probe 124 inside of the catheter 120 or endoscope is rotated across the surface of interest, cross-sectional images of one or more samples are obtained. In order to acquire three-dimensional data, the optical probe 124 is simultaneously translated longitudinally during the rotational spin resulting in a helical scanning pattern. This translation may be performed by pulling the tip of the probe 124 back towards the proximal end and therefore referred to as a pullback.

In one or more embodiments, the patient user interface 110 may comprise or include a connection component (or interface module), such as a rotary junction, to connect one or more components, such as one or more components of a probe (e.g., a catheter 120 (see e.g., FIGS. 1 and 3)), a needle, a capsule, a patient interface unit (e.g., the patient interface unit 110), etc., to one or more other components, such as, an optical component, a light source (e.g., the light source 101), a deflection section (e.g., such as the deflection or deflected section, which is a component that operates to deflect the light from the light source to the interference optical system, and then send light received from the interference optical system towards the at least one detector; a deflection or deflected section that includes at least one of: one or more interferometers, a circulator, a beam splitter, an isolator, a coupler, a fusion fiber coupler, a partially severed mirror with holes therein, and a partially severed mirror with a tap; etc.), the sample arm 102, a motor that operates to power the connection component and/or the patient user interface 110, etc. For example, when the connection member or interface module is a rotary junction, preferably the rotary junction operates as discussed below). In one or more other embodiments, the rotary junction may be at least one of: a contact rotary junction, a lenseless rotary junction, a lens-based rotary junction, or other rotary junction known to those skilled in the art.

In at least one embodiment, the PIU 110 may include a Fiber Optic Rotary Junction (FORJ), a rotational motor and translation motorized stage (e.g., a portion of the PIU 110), and a catheter connector (e.g., a portion of the PIU 110). The FORJ allows uninterrupted transmission of an optical signal while rotating a fiber along the fiber axis. The FORJ may have a free space optical beam combiner including a rotor and stator.

Descriptions of like-numbered elements present in the system 100' and already described above, such as for the system 100, shall not be repeated, and are incorporated by reference herein in their entireties.

In at least one embodiment, the console 1200, 1200' operates to control motions of a motor and translation motorized stage (hereinafter referred to as "motor" or "motor and stage"), acquires intensity data from the at least one detector(s) 107, and displays the scanned image (e.g., on a monitor or screen such as a display, screen or monitor 1209 as shown in the console 1200 of FIG. 10 and/or the console 1200' of FIG. 11 as further discussed below). In one or more embodiments, the console 1200, 1200' operates to change a speed of the motor and/or to stop the motor. The motor may be a stepping or a DC servo motor to control the speed and increase position accuracy.

In one or more embodiments, the console or computer 1200, 1200' operates to control the system 100 (and other systems, such as, but not limited to, the system 100', the system 100", the system 100''', etc. as discussed further below), the catheter 120 and/or one or more other above-described components of the system 100. In at least one embodiment, the console or computer 1200, 1200' operates to acquire intensity data from the at least one detector 107 of the OCT system/device/apparatus, and displays the image(s) (e.g., on a monitor or screen such as a display, screen or monitor 1209 as shown in the console 1200 of FIG. 10 and/or the console 1200' of FIG. 11 as further discussed below). The output of the one or more components of the system 100 (and other systems, such as, but not limited to, the system 100', the system 100", the system 100''', etc. as discussed further below) is acquired with the at least one detector 107 of the OCT system/device/apparatus, e.g., such as, but not limited to, photodiodes, Photomultiplier tube(s) (PMTs), line scan camera(s), or multi-array camera(s). Electrical analog signals obtained from the output of the system 100 (and/or other systems, such as, but not limited to, the system 100', the system 100", the system 100''', etc. as discussed further below) or one or more components thereof are converted to digital signals to be analyzed with a computer, such as, but not limited to, the computer 1200, 1200' and/or any other computer discussed herein (e.g., as shown in one or more of FIGS. 1-11). In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum. In some embodiments, the at least one detector 107 comprises three detectors configured to detect three different bands of light.

Figure 4:
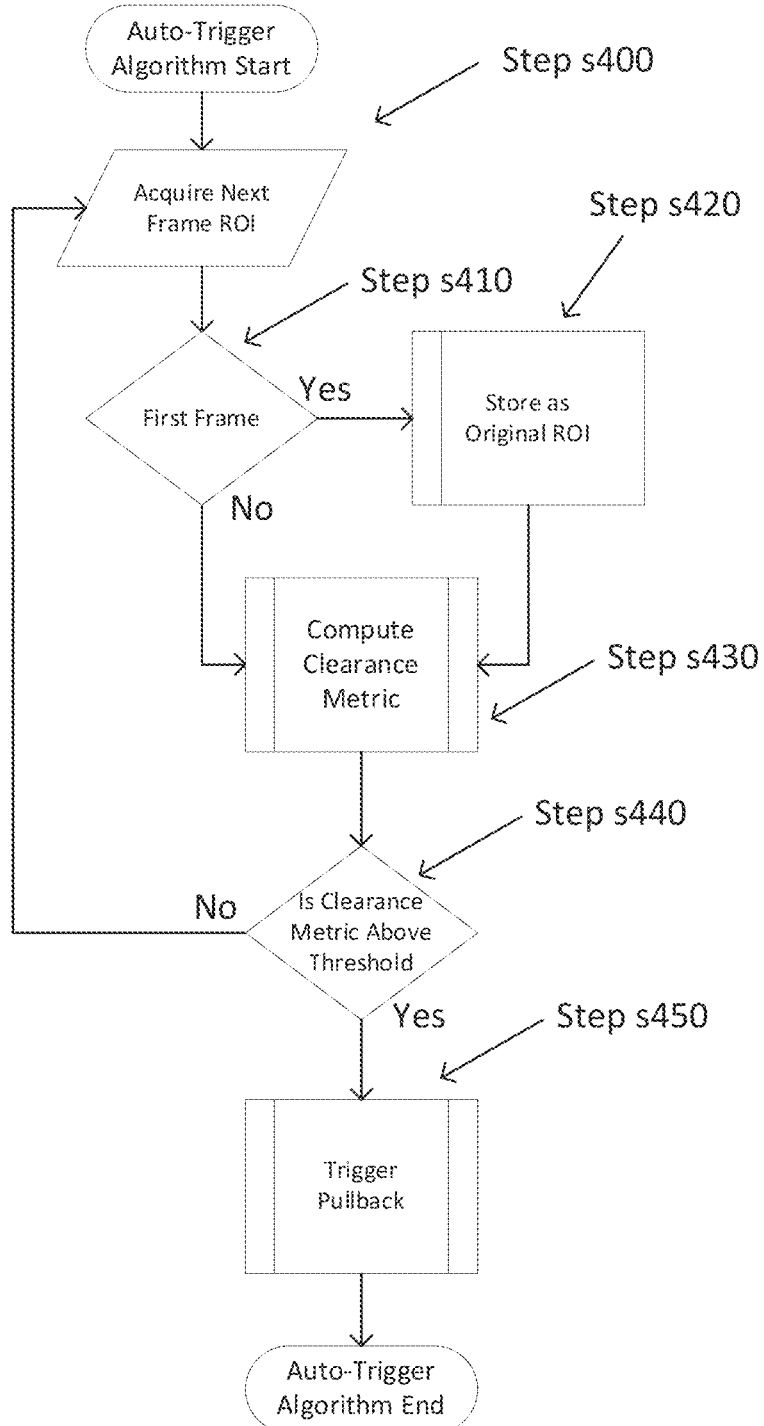
FIG. 4 is at least one embodiment of an auto-pullback trigger algorithm or method in accordance with one or more aspects of the present disclosure.
Figure 5:
FIGS. 5a-5c are images of at least one embodiment of an annulus that may be imaged in accordance with one or more aspects of the present disclosure.
Figure 5:
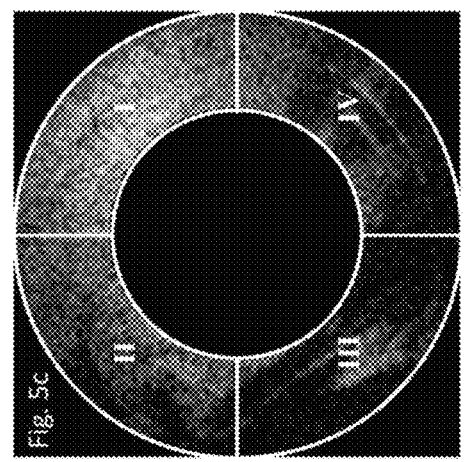
Figure 5:
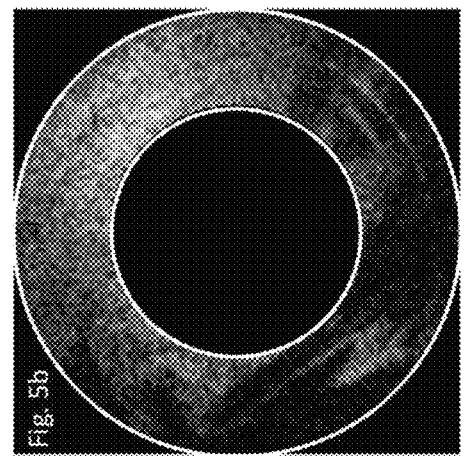

Now turning to the details of FIG. 4, at least one embodiment example of an auto-pullback triggering method (e.g., may be used at the onset of blood vessel clearance) is shown. For example, the OCT image is acquired at 200 frames per second and processed for display to the user at a substantially reduced rate 15-60 frames per second. Step s400 of the Auto-Trigger algorithm unit 230 receives an OCT frame from the data acquisition unit 220 at a rate of up to 200 frames per second and processes it in a number of ways. In an exemplary embodiment the data is already Fourier transformed and in this step a region of interest (ROI) is isolated in such a way that in the pre-scan conversion domain the data is selected such that only a band of the 2D images starting few pixels outside the catheter outer radius and extending for a depth equivalent to about the penetration depth in blood. In an example, the ROI is selected from about 90 pixels in depth to 160 pixels in depth and for all A-lines or from A-line 1 to A-line 500 in this example.

FIG. 5a shows the ROI as an annulus on the scan converted image of a partly cleared vessel image with overlaid annulus inner and outer rings, in this exemplary image, the inner ring diameter corresponds to about 0.9 mm, which is slightly larger than the catheter outer diameter of about 0.8 mm. the outer ring diameter corresponds to about 1.6 mm, which corresponds to a ring width of 0.35 mm, an approximate imaging depth of about up to 0.4 mm from the catheter outer edge. FIG. 5b shows a zoomed-in view of the annulus selection from FIG. 5a with a blacked out background for the image beyond the annulus. To optimize processing subsampling in the A-lines direction can be performed. For example every other A-line or one A-line for every three or more.

Step s410 of FIG. 4 identifies the first frame at start of the Auto-Trigger algorithm and stores the Reference ROI in memory, Step s420. Every subsequent frame ROI data is then directed to Step s430 where it is subtracted from the Reference ROI. This step ensures that substantially similar features are substantially subtracted from each other. This is an important step since catheter to lumen eccentricity can lead to a substantial part of the ROI be the vessel wall, guide wire, guide wire shadow, or other non-liquid (blood, flush media) structure. Pre and post blood clearance in this case may only minimally affect these regions and as such most of the signal change expected from blood clearance can be a minimal part of the whole change leading to smaller changes in the clearance metric. The clearance metric can in its simplest forms be the sum or mean value for 8-bit unsigned integer intensity values in the ROI of all subsequent frames.

Figure 6A:
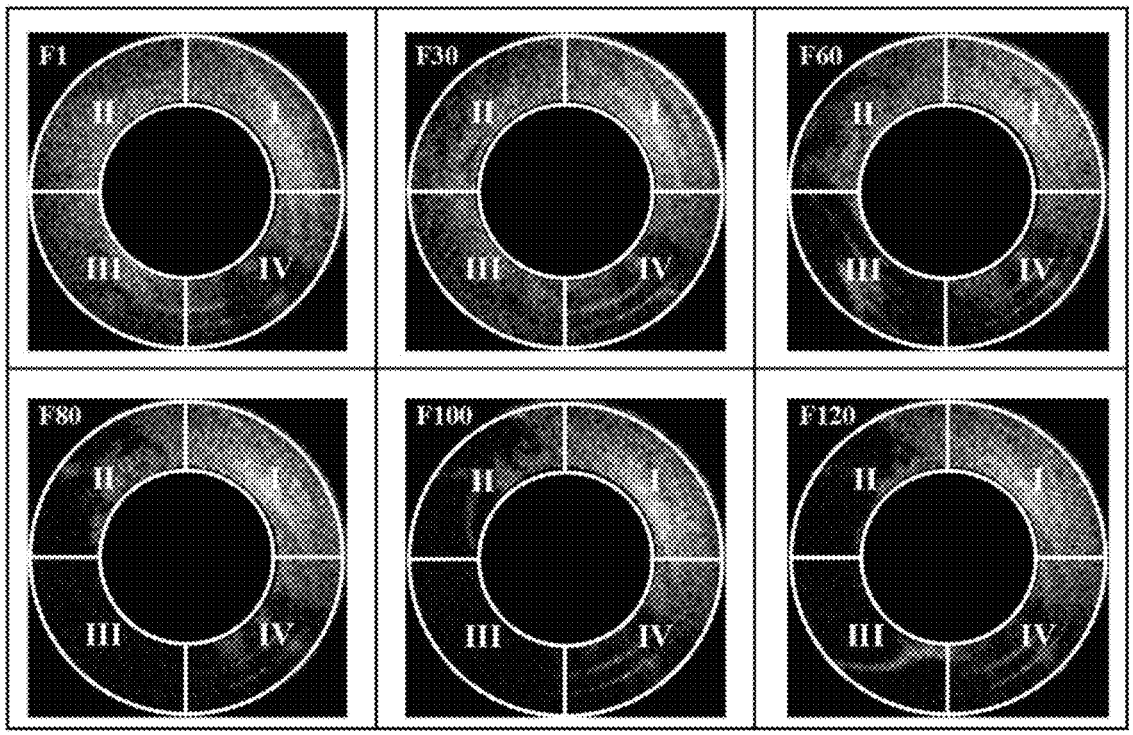
FIGS. 6A-6B are images of at least one embodiment depicting results of region of interest images and resulting signals, respectively, in accordance with one or more aspects of the present disclosure.

FIG. 6A shows results of original images ROI as they are acquired in Step s400 for several frames ranging from blood filled lumen, to partially clear lumen, to diagnostically clear vessel wall, where each figure is labeled with frame number after start of the algorithm. The clearance metric in another embodiment can be the sum or mean value for 8-bit unsigned integer intensity values in the ROI of all subsequent frames subtracted from the Reference ROI. The clearance metric in another embodiment can be the sum or mean value for 8-bit unsigned integer intensity values in the ROI of all subsequent frames subtracted from the Reference ROI then divided by the mean of the current frame ROI, or in another embodiment divided by the mean of the Reference ROI.

Step s440 can compare the value of the clearance metric to a pre-determined threshold value and trigger the pullback in Step s450 if the clearance metric is beyond the threshold or return to Step s400 and acquire a new frame ROI then go through the steps of the flow chart again. In another example the clearance metric is computed for n segments of the ROI, where n can be an integer value from 2 and up to half the number of processed A-lines in the ROI; preferably n can be in the range (4, 8).

Figure 6B:
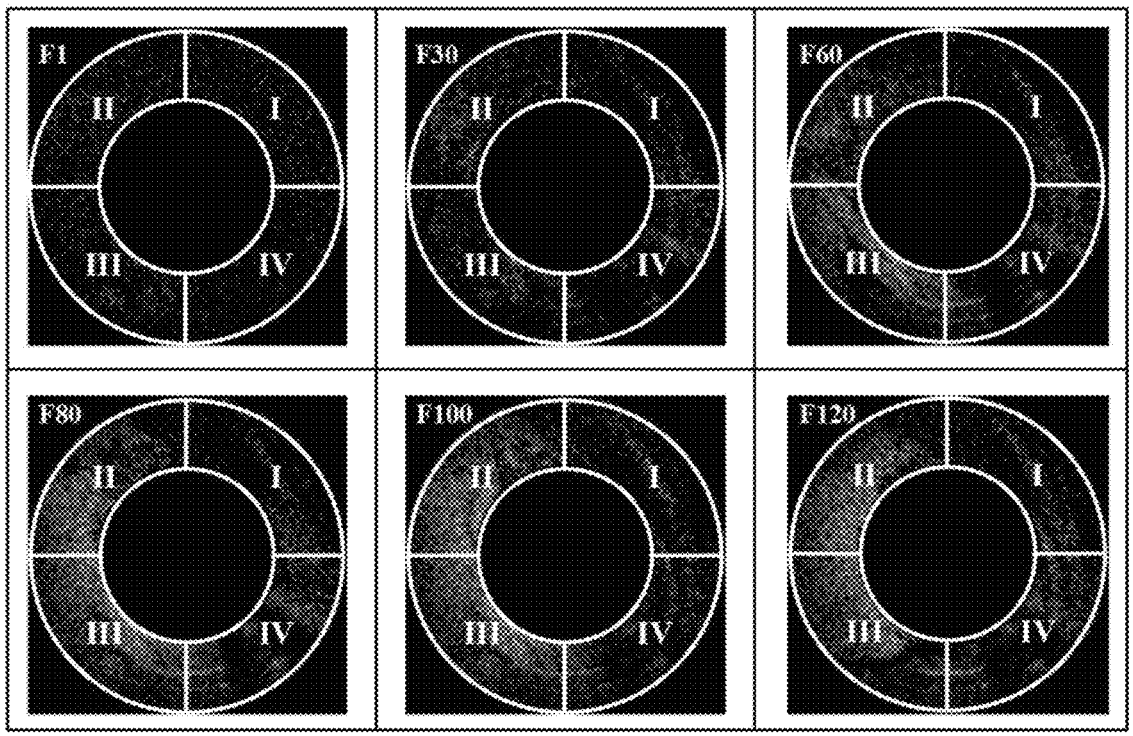

FIG. 5c shows the example where n=4. In this case, the first region is mostly vessel wall, region 2 is a mix of vessel wall and blood, region 3 is blood only, and region 4 is a mixture of blood, vessel wall, and guide wire. FIG. 6B shows the resultant signals from subtracting frames 1, 30, 60, 80, 100, and 120 from the reference frame respectively. Table 1 below shows resultant clearance metric which is measured three different ways. In an embodiment the resultant signals' mean ROI value can be used, or the resultant signals' mean ROI value relative to the mean ROI value from the reference frame ROI can be used, or the resultant signals' mean ROI value relative to the mean ROI value from the current frame ROI value can be used. In a preferred embodiment the region with the highest change is used, in this example as can be seen from the table below, region 3 has the largest change and can be used in Step s440 as the clearance metric to be compared to a set threshold. In other examples, one or more regions can be used with one or more thresholds to compare to.

TABLE 1

| Clearance Status Frame | Blood Obstructed 30 | | | | | Partly Clear 60 | | | | | Diagnostically Clear 80 | | | | |
| --- | --- | --- | --- | --- | --- | --- | --- | --- | --- | --- | --- | --- | --- | --- | --- |
| Region | Full | I | II | III | IV | Full | I | II | III | IV | Full | I | II | III | IV |
| ROI Mean | 16 | 10 | 21 | 16 | 15 | 24 | 11 | 28 | 38 | 20 | 32 | 12 | 43 | 50 | 25 |
| Relative to Reference (%) | 22 | 10 | 27 | 27 | 29 | 33 | 11 | 36 | 65 | 38 | 44 | 12 | 55 | 84 | 46 |
| Relative to Current (%) | 22 | 9 | 32 | 30 | 30 | 40 | 9 | 48 | 148 | 47 | 66 | 11 | 108 | 508 | 68 |

| | Clearance Status Frame | Diagnostically Clear 100 | | | | | Diagnostically Clear 120 | | | | |
| --- | --- | --- | --- | --- | --- | --- | --- | --- | --- | --- | --- |
| | Region | Full | I | II | III | IV | Full | I | II | III | IV |
| | ROI Mean | 34 | 13 | 52 | 51 | 20 | 31 | 15 | 46 | 42 | 23 |
| | Relative to Reference (%) | 47 | 13 | 67 | 86 | 38 | 43 | 15 | 59 | 71 | 43 |
| | Relative to Current (%) | 75 | 13 | 181 | 605 | 49 | 67 | 14 | 162 | 266 | 57 |

A threshold can be set so that pullback is triggered after partial clearing or only after diagnostic clearing is achieved. The value can be set to optimize pullback such as if the time it takes from issuance of the trigger pullback by the Auto-Trigger algorithm and the actual motion of the pullback mechanism is in the tens of milliseconds range then the threshold value could be set high and the clearance metric will only exceed it for what is equivalent to a diagnostically clear image. However, if such delay is larger than 100 milliseconds then the threshold value could be set low and the clearance metric will exceed it for what is equivalent to partly clear image.

In certain embodiment where the system requires saving raw photodetector signals it might be difficult for standard computers to real time process the raw signals especially for the case of systems using two detection channels into A-lines which may involve obtaining FFT of 50 to 200 thousand A-lines per second and even MHz rate. In this case the computer can take advantage of modern digitizers that have built-in FPGA for controlling data flow that are capable of OCT processing, including but not limited to windowing of the data, zero-padding, Fast Fourier Transform (FFT), magnitude calculation, and taking the logarithm of the result before issuance of the Trigger Pullback signal. After the issuance of such signal one can then switch to transferring raw data from the digitizer and saving and processing it at a much lower rate than it was acquired.

Additionally in case of systems with two detection channels one might use a single channel for faster processing data before issuance of Trigger Pullback signal. After the issuance of such signal one can then switch to processing data from both channels.

In a separate embodiment one may keep track of the clearance metric for more than one frame and have a preliminary threshold for Pre-Trigger that is indicative of a partial clearing and once the Trigger Pullback threshold is reached start Trigger Pullback only if the clearance metric has exceeded the pre-trigger threshold for a certain minimum number of frames, one or more. If not, a number of consecutive frames, one or more shall have the clearance metric exceed the Trigger Pullback threshold before issuing the Trigger Pullback signal.

In a certain embodiment, the reference frame could be captured in low rotation speed mode and adjusted to match the ROI for frames used in the Auto-Trigger algorithm. Such frame could be used in lieu of the first frame for Step s400 as the reference ROI if it occurs that the values from the reference frame are indicative of a possible preclearing image as in the case where contrast was administered by mistake sooner than the system was put in pre-record/pullback mode.

While the present invention has been described with reference to exemplary embodiments, it is to be understood that the invention is not limited to the disclosed exemplary embodiments. The scope of the claims is to be accorded the broadest interpretation so as to encompass all modifications, equivalent structures, and functions.

A computer, such as the console or computer 1200, 1200', may perform any of the steps, processes, and/or techniques discussed herein for any apparatus and/or system being manufactured or used, any of the embodiments shown in FIGS. 1-11, any other apparatus or system discussed herein, etc.

Figure 7:
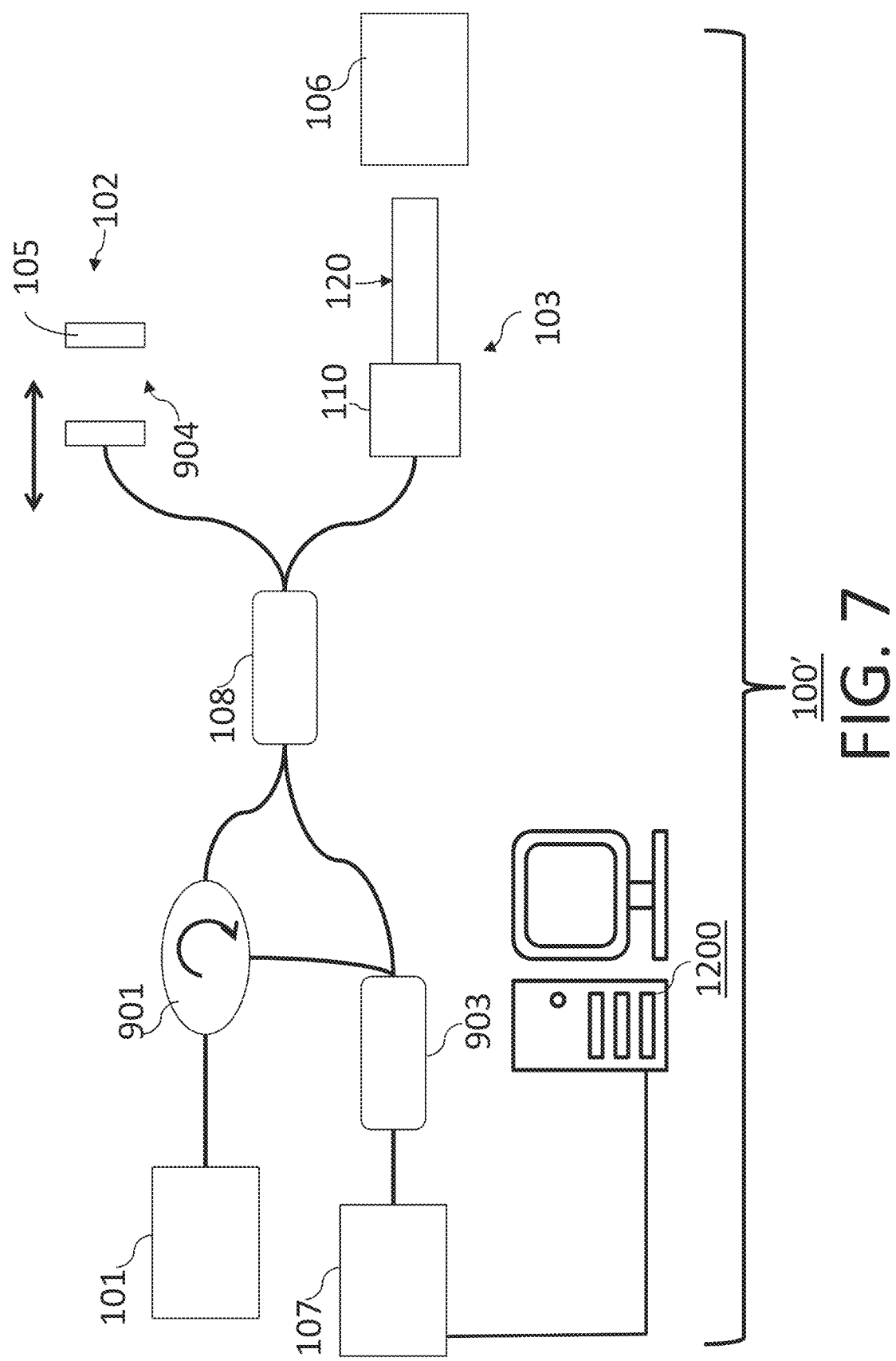
FIG. 7 is a diagram showing an embodiment of at least an additional system which can utilize one or more auto-pullback trigger techniques in accordance with one or more aspects of the present disclosure.

In accordance with one or more further aspects of the present disclosure, bench top systems may be utilized with the lumen edge and artifact(s) detection OCT techniques disclosed herein. FIG. 7 shows an example of a system that can utilize the lumen edge and artifact(s) detection OCT techniques for a bench-top such as for ophthalmic applications. A light from a light source 101 delivers and splits into a reference arm 102 and a sample arm 103 with a deflecting (or deflection) section 108. A reference beam goes through a length adjustment section 904 (which is optional in one or more embodiments) and is reflected from a reference mirror (such as reference mirror or reference reflection 105 shown in FIG. 1) in the reference arm 102 while a sample beam is reflected or scattered from a sample, target or object 106 in the sample arm 103 (e.g., via the PIU 110 and the catheter 120). In one embodiment, both beams combine at the deflecting/deflection section 108 and generate interference patterns. In one or more embodiments, the beams go to the combiner 903, and the combiner 903 combines both beams via the circulator 901 and the deflecting section 108. The combined beams preferably are delivered to one or more detectors (such as the one or more detectors 107). The output of the beam splitter (see e.g., beam splitter 104 in FIG. 1), the deflecting section 108, and/or an interferometer is continuously acquired with one or more detectors, such as the one or more detectors 107. The electrical analog signals are converted to the digital signals to analyze them with a computer, such as, but not limited to, the computer 1200 (see FIG. 1; also shown in FIGS. 7-9 and 10 discussed further below), the computer 1200' (see e.g., FIG. 11 discussed further below), etc.

Figure 8:
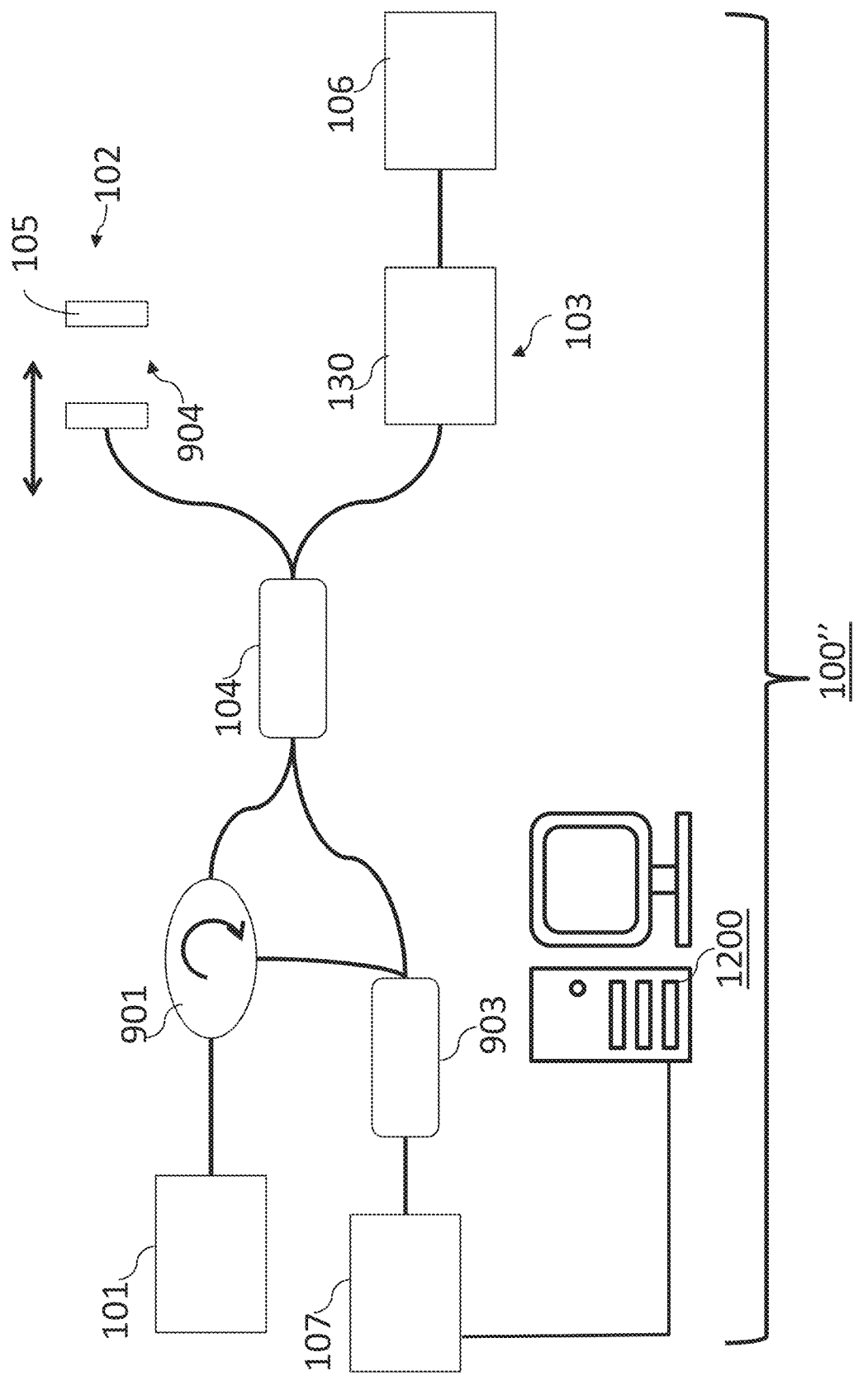
FIG. 8 is a diagram showing an embodiment of at least another system which can utilize one or more auto-pullback trigger techniques in accordance with one or more aspects of the present disclosure.

In one or more embodiments, the sample arm 103 may include a phase shift unit 103 for a bench top system(s) as shown in system 100" in FIG. 8. The sample 106 may be located at the place of the mirror 105 used with the phase shift unit 130 (e.g., as shown in FIG. 1). A light from a light source 101 delivers and splits into a reference arm 102 and a sample arm 103 with a splitter 104. A reference beam goes through a length adjustment section 904 and is reflected from a reference mirror (such as reference mirror 105 shown in FIG. 1) in the reference arm 102 while a sample beam is reflected or scattered from a sample, target and/or object 106 through a phase shift unit (such as the phase shift unit 130) in the sample arm 103. In one embodiment, both beams combine at the splitter 104 and generate interference patterns. In one or more embodiments, the beams go to the combiner 903, and the combiner 903 combines both beams via the circulator 901 and the splitter 104, and the combined beams are delivered to one or more detectors (such as the one or more detectors 107). The output of the beam splitter 104 and/or an interferometer is continuously acquired with one or more detectors, such as the one or more detectors 107. The electrical analog signals are converted to the digital signals to analyze them with a computer.

There are many ways to compute rotation, intensity, lumen distance, or any other measurement discussed herein, to perform auto-pullback method(s) or algorithm(s), and/or to control and/or manufacture an MMOCT device/apparatus, system and/or storage medium, digital as well as analog. In at least one embodiment, a computer, such as the console or computer 1200, 1200', may be dedicated to control and/or use OCT devices, systems, methods and/or storage mediums for use therewith described herein.

Figure 9:
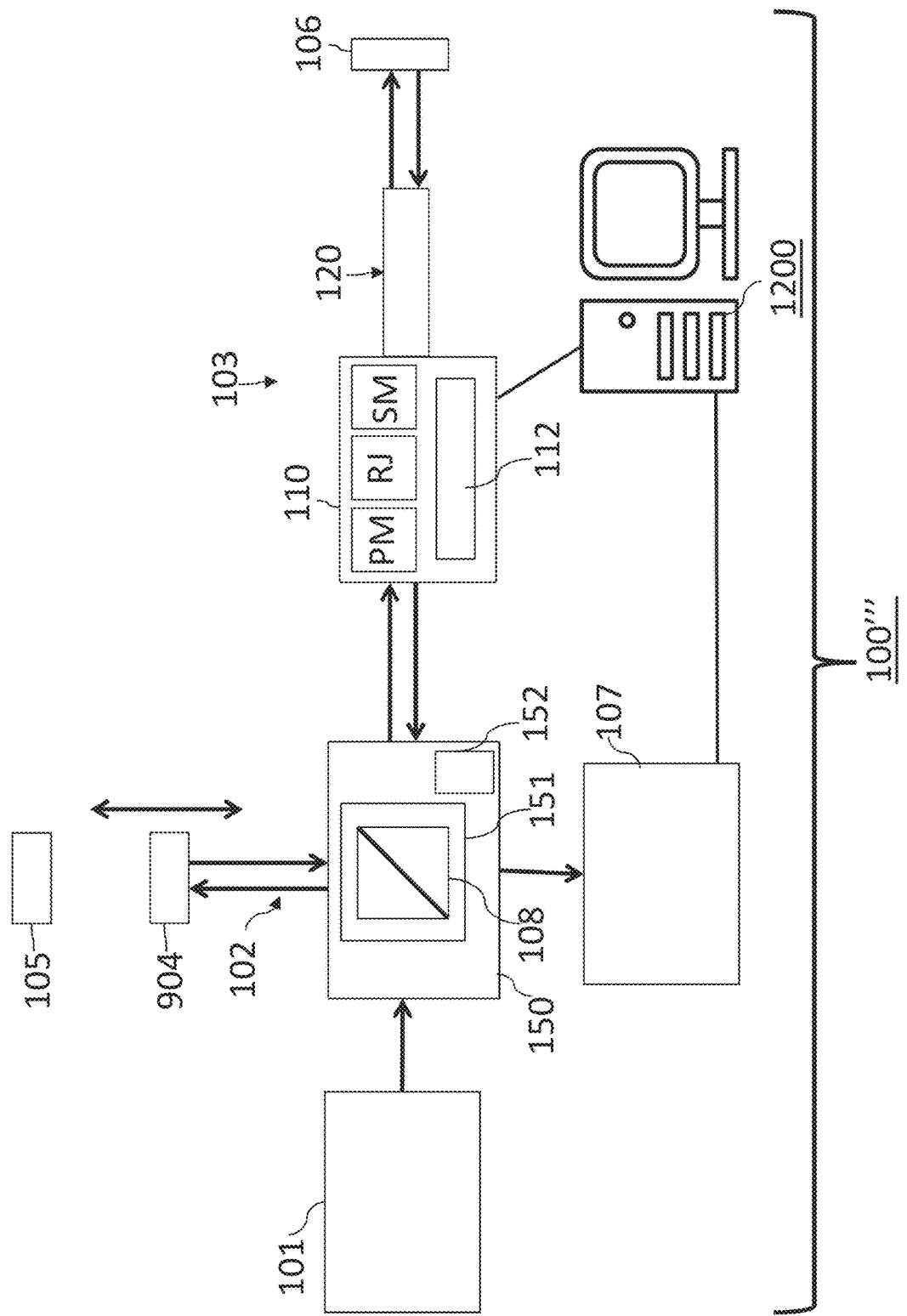
FIG. 9 is a diagram showing an embodiment of at least a further system which can utilize one or more auto-pullback trigger techniques in accordance with one or more aspects of the present disclosure.

In accordance with one or more further aspects of the present disclosure, one or more other systems may be utilized with the lumen edge and artifact(s) detection OCT techniques disclosed herein. FIG. 9 shows an example of a system 100''' that may utilize the lumen edge and artifact(s) detection OCT techniques such as for ophthalmic applications. A light from a light source 101 delivers and splits into a reference arm 102 and a sample arm 103 with a deflecting section 108 (e.g., a beam splitter or other deflecting or deflected section discussed herein) located inside of an OCT imaging engine 150, which may also include an OCT interferometer 151 (which may house or include the deflecting section 108) and a swept source engine 152 in one or more embodiments. A reference beam may pass through a length adjustment section 904, which may operate to change the distance of a reference mirror (such as reference mirror or reference reflection 105; also shown in FIG. 1) and is reflected from the reference reflection 105 in the reference arm 102 while a sample beam is reflected or scattered from a sample, target or object 106 in the sample arm 103. In one embodiment, both beams combine at the deflecting section 108 and generate interference patterns. In one or more embodiments, the combined beams are delivered to one or more detectors. The output of the interferometer 151 is continuously acquired with one or more detectors, such as the one or more detectors 107. The electrical analog signals are converted to the digital signals to analyze them with a computer, such as, but not limited to, the computer 1200 (see FIG. 9; also shown in FIG. 10 discussed further below), the computer 1200' (see e.g., FIG. 11 discussed further below), etc. In one or more embodiments, the sample arm 103 includes the PIU 110 and the catheter 120 so that the sample beam is reflected or scattered from the sample, target or object 106 as discussed herein. In one or more embodiments, the PIU 110 may include one or more motors to control the pullback operation of the catheter 120 (or one or more components thereof) and/or to control the rotation or spin of the catheter 120 (or one or more components thereof). For example, the PIU 110 may include a pullback motor (PM) and a spin motor (SM), and/or may include a motion control unit 112 that operates to perform the pullback and/or rotation features using the pullback motor PM and/or the spin motor SM. As discussed herein, the PIU 110 may include a rotary junction (e.g., rotary junction RJ as shown in FIG. 9). The rotary junction RJ may be connected to the spin motor SM so that the catheter 120 may obtain one or more views or images of the sample 106. The computer 1200 (or the computer 1200') may be used to control one or more of the pullback motor PM, the spin motor SM and/or the motion control unit 112. An OCT system may include one or more of the OCT engine 150, a computer (e.g., the computer 1200, the computer 1200', etc.), the PIU 110, the catheter 120, a monitor, etc. One or more embodiments of an OCT system may interact with one or more external systems, such as, but not limited to, an angio system, external displays, one or more hospital networks, external storage media, a power supply, a bedside controller (e.g., which may be connected to the OCT system using Bluetooth technology or other methods known for wireless communication), etc.

Unless otherwise discussed herein, like numerals indicate like elements. For example, while variations or differences exist between the systems, such as, but not limited to, the system 100, the system 100', the system 100", the system 100''', etc. (e.g., differences between the position(s) of the reference reflection 105 (and/or reference arm 102) depending on the OCT system or method being used), one or more features thereof may be the same or similar to each other, such as, but not limited to, the light source 101, the deflecting section 108 or other component(s) thereof (e.g., the console 1200, the console 1200', etc.). Those skilled in the art will appreciate that the light source 101, the at least one detector 107 and/or one or more other elements of the system 100, may operate in the same or similar fashion to those like-numbered elements of one or more other systems, such as, but not limited to, the system 100', the system 100", the system 100''', etc. as discussed herein. Those skilled in the art will appreciate that alternative embodiments of the system 100, the system 100', the system 100", the system 100''', and/or one or more like-numbered elements of one of such systems, while having other variations as discussed herein, may operate in the same or similar fashion to the like-numbered elements of any of the other systems (or component(s) thereof) discussed herein. Indeed, while certain differences exist between the system 100, the system 100', the system 100" and the system 100''', as discussed herein, there are similarities between the systems discussed herein. Likewise, while the console or computer 1200 may be used in one or more systems (e.g., the system 100, the system 100', the system 100", the system 100''', etc.), one or more other consoles or computers, such as the console or computer 1200', may be used additionally or alternatively.

The one or more detectors of the apparatus or system embodiments (e.g. of the system of FIG. 1, the system of FIG. 2, or any other system discussed herein) may transmit the digital or analog signals to a processor or a computer such as, but not limited to, an image processor, a processor or computer 1200, 1200' (see e.g., FIGS. 1 and 7-11), a combination thereof, etc. The image processor may be a dedicated image processor or a general purpose processor that is configured to process images. In at least one embodiment, the computer 1200, 1200' may be used in place of, or in addition to, the image processor. In an alternative embodiment, the image processor may include an ADC and receive analog signals from the one or more detectors of the OCT system 100. The image processor may include one or more of a CPU, DSP, FPGA, ASIC, or some other processing circuitry. The image processor may include memory for storing image, data, and instructions. The image processor may generate one or more images based on the information provided by the one or more detectors 107. A computer or processor discussed herein, such as, but not limited to, a processor of the devices, apparatuses or systems of FIGS. 1-11, the computer 1200, the computer 1200', the image processor, may also include one or more components further discussed herein below (see e.g., FIGS. 10-11).

The output of the one or more components of any of the systems discussed herein may be acquired with the at least one detector, e.g., such as, but not limited to, photodiodes, Photomultiplier tube(s) (PMTs), line scan camera(s), or multi-array camera(s). Electrical analog signals obtained from the output of the system of FIG. 1 or the detector(s) thereof, and/or from the devices, apparatuses, or systems of FIGS. 1-11, are converted to digital signals to be analyzed with a computer, such as, but not limited to, the computer of FIG. 1, the computer of FIG. 2, the computer 1200, 1200', etc. In one or more embodiments, a light source of the OCT system 100 may be a radiation source or a broadband light source that radiates in a broad band of wavelengths. In one or more embodiments, a Fourier analyzer including software and electronics may be used to convert the electrical analog signals into an optical spectrum.

There are many ways to compute power and/or detect lumen edge(s) and artifact(s), and/or perform auto-pullback method(s) or algorithm(s), digital as well as analog. In at least one embodiment, a computer, such as the computer of FIG. 1, the computer of FIG. 2, the console or computer 1200, 1200', etc., may be dedicated to the control and the monitoring of the OCT devices, systems, methods and/or storage mediums described herein.

The electric signals used for imaging may be sent to one or more processors, such as, but not limited to, the computer of FIG. 1, the computer of FIG. 2, a computer 1200 (see e.g., FIG. 10), a computer 1200' (see e.g., FIG. 11), etc. as discussed further below, via cable(s) or wire(s), such as, but not limited to, the cable(s) or wire(s) 113 (see FIG. 1). Additionally or alternatively, the computers or processors discussed herein are interchangeable, and may operate to perform any of the feature(s) and method(s) discussed herein.

Figure 10:
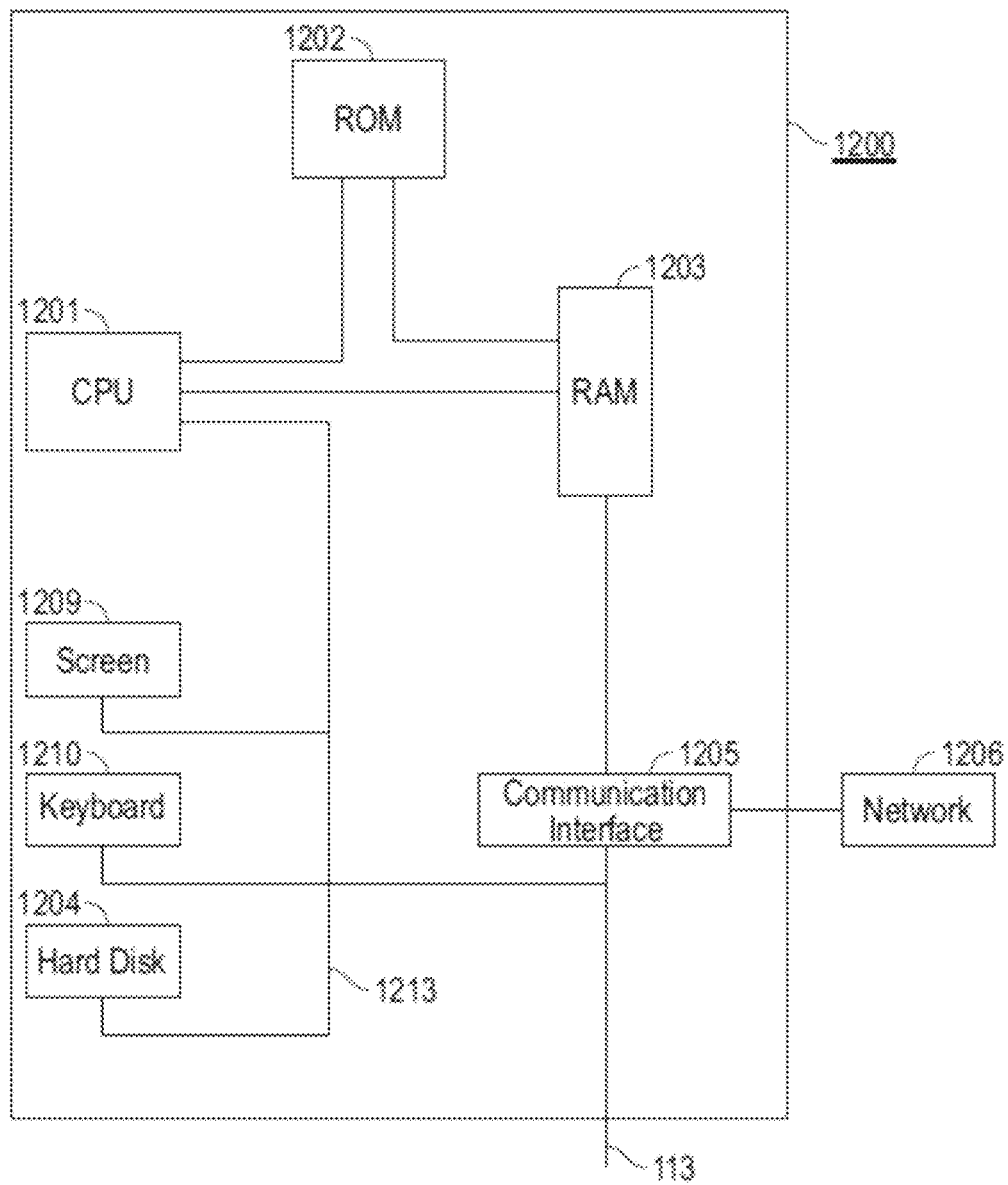
FIG. 10 shows a schematic diagram of an embodiment of a computer that may be used with one or more embodiments of an apparatus or system or one or more methods discussed herein in accordance with one or more aspects of the present disclosure.

Various components of a computer system 1200 (see e.g., the console or computer 1200 as may be used as one embodiment example of the computer shown in FIG. 1) are provided in FIG. 10. A computer system 1200 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS (or "Bus") or other connection lines (e.g., connection line 1213) between one or more of the aforementioned components (e.g., as shown in FIG. 10). In addition, the computer system 1200 may comprise one or more of the aforementioned components. For example, a computer system 1200 may include a CPU 1201, a RAM 1203, an input/output (I/O) interface (such as the communication interface 1205) and a bus (which may include one or more lines 1213 as a communication system between components of the computer system 1200; in one or more embodiments, the computer system 1200 and at least the CPU 1201 thereof may communicate with the one or more aforementioned components of a FORJ or a device or system using same, such as, but not limited to, the system 100, the system 100', the system 100", the system 100''', and/or the systems/apparatuses of FIGS. 1-11, discussed herein above, via one or more lines 1213), and one or more other computer systems 1200 may include one or more combinations of the other aforementioned components (e.g., the one or more lines 1213 of the computer 1200 may connect to other components via line 113). The CPU 1201 is configured to read and perform computer-executable instructions stored in a storage medium. The computer-executable instructions may include those for the performance of the methods and/or calculations described herein. The computer system 1200 may include one or more additional processors in addition to CPU 1201, and such processors, including the CPU 1201, may be used for controlling and/or manufacturing a device, system or storage medium for use with same or for use with any lumen detection, stent(s) detection, artifact(s) detection, and/or lumen distance calculation technique(s), and/or use with auto-pullback technique(s) discussed herein. The system 1200 may further include one or more processors connected via a network connection (e.g., via network 1206). The CPU 1201 and any additional processor being used by the system 1200 may be located in the same telecom network or in different telecom networks (e.g., performing, manufacturing, controlling, calculation, and/or using technique(s) may be controlled remotely).

Figure 11:
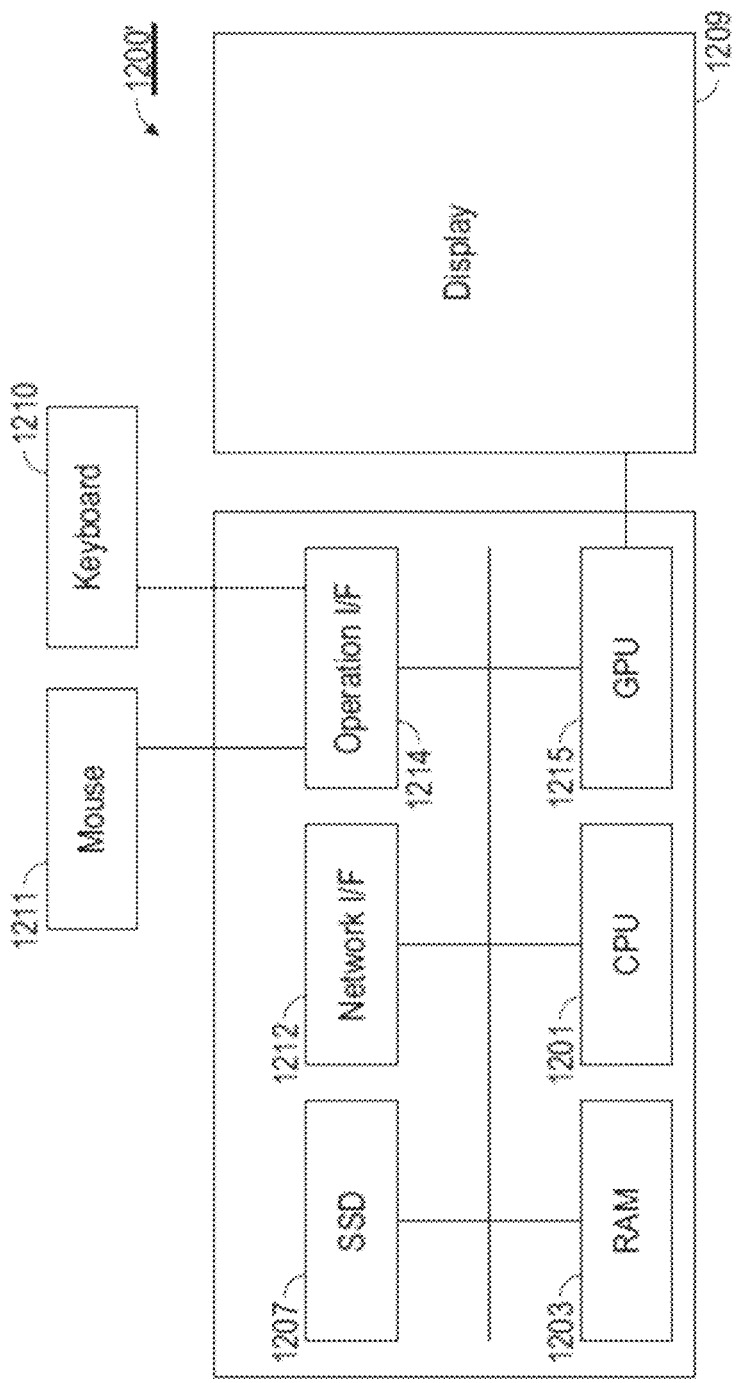
FIG. 11 shows a schematic diagram of another embodiment of a computer that may be used with one or more embodiments of an imaging apparatus or system or methods discussed herein in accordance with one or more aspects of the present disclosure.

The I/O or communication interface 1205 provides communication interfaces to input and output devices, which may include the light source 101, a RJ, a PM, an SM, unit 150, unit 112, a microphone, a communication cable and a network (either wired or wireless), a keyboard 1210, a mouse (see e.g., the mouse 1211 as shown in FIG. 11), a touch screen or screen 1209, a light pen and so on. The communication interface of the computer 1200 may connect to other components discussed herein via line 113 (as diagrammatically shown in FIG. 10). The Monitor interface or screen 1209 provides communication interfaces thereto.

Any methods and/or data of the present disclosure, such as, but not limited to, the methods for using and/or manufacturing a device, system or storage medium for use with same and/or method(s) for imaging, performing tissue or sample characterization or analysis, performing diagnosis, planning and/or examination, detecting lumen edge(s), stent(s), and/or artifact(s), including in OCT image(s), and/or for performing auto-pullback technique(s), as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-Ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1207 in FIG. 11), SRAM, etc.), an optional combination thereof, a server/database, etc. may be used to cause a processor, such as, the processor or CPU 1201 of the aforementioned computer system 1200 to perform the steps of the methods disclosed herein. The computer-readable storage medium may be a non-transitory computer-readable medium, and/or the computer-readable medium may comprise all computer-readable media, with the sole exception being a transitory, propagating signal in one or more embodiments. The computer-readable storage medium may include media that store information for predetermined, limited, or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, devices, systems, and computer-readable storage mediums related to the processors, such as, but not limited to, the processor of the aforementioned computer 1200, the processor of computer 1200', etc., as described above may be achieved utilizing suitable hardware, such as that illustrated in the figures. Functionality of one or more aspects of the present disclosure may be achieved utilizing suitable hardware, such as that illustrated in FIG. 10. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201 (as shown in FIG. 10 or FIG. 11, and/or which may be included in the computer of FIG. 1) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented byway of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium. The computers or processors (e.g., 2, 1200, 1200', etc.) may include the aforementioned CPU structure, or may be connected to such CPU structure for communication therewith.

As aforementioned, hardware structure of an alternative embodiment of a computer or console 1200' is shown in FIG. 11. The computer 1200' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid-state drive (SSD) 1207. Preferably, the computer or console 1200' includes a display 1209. The computer 1200' may connect with one or more components of a system (e.g., the systems/apparatuses of FIGS. 1-11, etc.) via the operation interface 1214 or the network interface 1212. A computer, such as the computer 1200, 1200' or the computer of FIG. 1, may include a rotary joint/junction RJ, a motor, etc. in one or more embodiments. The operation interface 1214 is connected with an operation unit such as a mouse device 1211, a keyboard 1210 or a touch panel device. The computer 1200' may include two or more of each component. Alternatively, the CPU 1201 or the GPU 1215 may be replaced by the field-programmable gate array (FPGA), the application-specific integrated circuit (ASIC) or other processing unit depending on the design of a computer, such as the computer 1200, the computer 1200', etc.

At least one computer program is stored in the SSD 1207, and the CPU 1201 loads the at least one program onto the RAM 1203, and executes the instructions in the at least one program to perform one or more processes described herein, as well as the basic input, output, calculation, memory writing, and memory reading processes.

The computer, such as the computer 1200, 1200', the computer of FIG. 1, etc., communicates with the one or more components of the apparatuses/systems of FIGS. 1-11, to perform imaging, and reconstructs an image from the acquired intensity data. The monitor or display 1209 displays the reconstructed image, and may display other information about the imaging condition or about an object to be imaged. The monitor 1209 also provides a graphical user interface for a user to operate a system, for example when performing OCT or other imaging technique, including, but not limited to, detection of lumen edge(s) and/or artifact(s), and/or performing auto-pullback technique(s). An operation signal is input from the operation unit (e.g., such as, but not limited to, a mouse device 1211, a keyboard 1210, a touch panel device, etc.) into the operation interface 1214 in the computer 1200', and corresponding to the operation signal the computer 1200' instructs the system (e.g., the system 100, the system 100', the system 100", the system 100''', the systems/apparatuses of FIGS. 1-11, etc.) to set or change the imaging condition, and to start or end the imaging, and/or to start or end the lumen detection, stent(s) detection, artifact(s) detection, blood clearance detection and/or performance of auto-pullback technique(s). The laser source 101 of an OCT system as aforementioned may have interfaces to communicate with the computers 1200, 1200' to send and receive the status information and the control signals.

Similarly, the present disclosure and/or one or more components of devices, systems and storage mediums, and/or methods, thereof also may be used in conjunction with optical coherence tomography probes.

Such probes include, but are not limited to, the OCT imaging systems disclosed in U.S. Pat. Nos. 6,763,261; 7,366,376; 7,843,572; 7,872,759; 8,289,522; 8,676,013; 8,928,889; 9,087,368; 9,557,154; and U.S. Pat. Pub. Nos. 2014/0276011 and 2017/0135584; and WO 2016/015052 to Tearney et al. and arrangements and methods of facilitating photoluminescence imaging, such as those disclosed in U.S. Pat. No. 7,889,348 to Tearney et al., as well as the disclosures directed to multimodality imaging disclosed in U.S. Pat. No. 9,332,942, and U.S. Patent Publication Nos. 2010/0092389, 2011/0292400, 2012/0101374, 2016/0228097, 2018/0045501, and 2018/0003481, each of which patents, patent publications and patent application(s) are incorporated by reference herein in their entireties. As aforementioned, any feature or aspect of the present disclosure may be used with the features disclosed in WO 2016/144878, which is incorporated by reference herein in its entirety. As aforementioned, any feature or aspect of the present disclosure may be used with OCT imaging systems, apparatuses, methods, storage mediums or other aspects or features as discussed in U.S. Pat. Pub. 2019/0298174; U.S. patent application Ser. No. 16/131,662; U.S. patent application Ser. No. 16/414,222, filed on May 16, 2019; U.S. Pat. App. No. 62/901,472; U.S. Pat. App. No. 62/925,655; and U.S. Pat. App. No. 62/944,064, filed on Dec. 5, 2019, each of which patent(s), publication(s) and application(s) are incorporated by reference herein in their entireties.

Although the disclosure herein has been described with reference to particular embodiments, it is to be understood that these embodiments are merely illustrative of the principles and applications of the present disclosure (and are not limited thereto), and the invention is not limited to the disclosed embodiments. It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications, equivalent structures, and functions.

The invention claimed is:

1. An imaging device for triggering an automatic pullback, the imaging device comprising:
one or more processors that operate to:
collect image data from an object, target, or sample, and obtain or identify a reference frame for a region of interest (ROI) in the image data;
determine an amount of a change in an image intensity of each of one or more other frames of the image data showing the region of interest (ROI) relative to an image intensity of the region of interest (ROI) shown or as in the reference frame;
determine whether the amount of, or a level in, the change for each of the one or more other frames of the image data showing the region of interest (ROI) indicates that a partial clearing or a diagnostic clearing of the object, target, or sample is or has been achieved where a clearance metric is above a threshold; and issue a signal based on the determined amount of, or the change indicating that the partial clearing or the diagnostic clearing of the object, target, or sample is or has been achieved and based on the clearance metric being above the threshold, the signal operating to trigger the automatic pullback.

2. The imaging device of claim 1, wherein the one or more processors further operate to one or more of the following:
  (i) acquire a next frame of the region of interest (ROI);
  (ii) isolate the region of interest (ROI) such that in a pre-scan conversion domain data is selected such that a band of two-dimensional (2D) images start a few pixels outside an outer radius of a catheter and extend for a depth equivalent to about a light penetration depth in blood;
  (iii) receive one or more imaging modality frames at a rate of up to 200 frames per second;
  (iv) select the region of interest (ROI) from about 90 pixels in depth to 160 pixels in depth and for either all A-lines of an image or frame or from A-line 1 to A-line 500 of the image or frame;
  (v) capture the reference frame in a low rotation speed mode for a catheter of the imaging device and/or for the imaging device and adjust the reference frame to match the region of interest (ROI) for frames used to detect the automatic pullback trigger;
  (vi) capture the reference frame in a low rotation speed mode for a catheter of the imaging device and/or for the imaging device and adjust the reference frame to match the of interest (ROI) for frames used to detect the automatic pullback trigger, and use the region of interest (ROI) shown or as in the reference frame as a reference region of interest (ROI), instead of acquiring the next frame region of interest (ROI), where values from the reference frame are indicative of or show a possible preclearing image; and/or
  (vii) determine whether a possible preclearing image includes a case where contrast is or was administered by mistake before the imaging device was put in a pre-record mode and/or a pullback mode.

3. The imaging device of claim 1, wherein the one or more processors further operate to one or more of the following:
  (i) process or display the region of interest (ROI) as an annulus on a scan converted image of the object, target, or sample being a partly cleared vessel image with overlaid annulus inner and outer rings;
  (ii) process or display the region of interest (ROI) with a blacked out background for the image beyond an annulus;
  (iii) perform subsampling in the A-lines direction to improve or optimize processing; and/or
  (iv) process the subsampling every other A-line or one A-line for every three or more A-lines.

4. The imaging device of claim 1, wherein the one or more processors further operate to one or more of the following:
  (i) acquire a next frame of the region of interest (ROI), or use the region of interest (ROI) shown or as in the reference frame as a reference region of interest (ROI) where values from the reference frame are indicative of a possible preclearing image;
  (ii) identify a first frame of the region of interest (ROI);
  (iii) store the first frame as an original image of the region of interest (ROI);
  (iv) store the first frame as an original image of the region of interest (ROI) in a memory;
  (v) compute or determine the clearance metric, the clearance metric including a comparison of data, or intensity value(s), for one or more frames of the region of interest (ROI) with data, or intensity value(s), for the reference frame, or the clearance metric operating to measure the amount of, or the level in, the change; and/or
  (vi) in the event that the clearance metric is not above the threshold, then return to acquire a next frame of the region of interest (ROI), and compute or determine a new clearance metric until the clearance metric is above the threshold.

5. The imaging device of claim 4, wherein the one or more processors further operate to one or more of the following:
  (i) where the region of interest (ROI) shown or as in the reference frame is used as a reference region of interest (ROI) and where values from the reference frame are indicative of a possible preclearing image, subtract every subsequent frame region of interest (ROI) data from the reference region of interest (ROI);
  (ii) where the region of interest (ROI) shown or as in the reference frame is used as a reference region of interest (ROI) and where values from the reference frame are indicative of a possible preclearing image, subtract every subsequent frame region of interest (ROI) data from the reference region of interest (ROI) such that substantially similar features or the same features are substantially subtracted or are subtracted from each other;
  (iii) calculate or determine the clearance metric to be one or more of the following: a sum or mean value for 8-bit unsigned integer values in the region of interest (ROI) of all subsequent frames, a sum or mean value for 8-bit unsigned integer intensity values in region of interest (ROI) data of all subsequent frames subtracted from a reference region of interest (ROI) where the region of interest (ROI) shown or as in the reference frame is used as the reference region of interest (ROI) and where values from the reference frame are indicative of a possible preclearing image such that the subtraction produces a resultant signal, a sum or mean value for 8-bit unsigned integer intensity values in region of interest (ROI) data of all subsequent frames subtracted from a reference region of interest (ROI) then divided by a mean of a current frame region of interest (ROI) in a case where the region of interest (ROI) shown or as in the reference frame is used as the reference region of interest (ROI) and where values from the reference frame are indicative of a possible preclearing image such that the subtraction produces a resultant signal, a sum or mean value for 8-bit unsigned integer intensity values in region of interest (ROI) data of all subsequent frames subtracted from a reference region of interest (ROI) then divided by the mean of the reference region of interest (ROI) where the region of interest (ROI) shown or as in the reference frame is used as the reference region of interest (ROI) and where values from the reference frame are indicative of a possible preclearing image such that the subtraction produces a resultant signal, a mean region of interest (ROI) value of a resultant signal generated by subtracting region of interest (ROI) data of one or more frames from a reference region of interest (ROI), a mean region of interest (ROI) value of a resultant signal generated by subtracting region of interest (ROI) data of one or more frames from a reference region of interest (ROI) relative to a mean region of interest (ROI) value from the region of interest (ROI) shown or as in the reference frame, a mean ROI region of interest (ROI) value of a resultant signal generated by subtracting region of interest (ROI) data of one or more frames from a reference region of interest (ROI) relative to a mean region of interest (ROI) value from a region of interest (ROI) value of a current frame, a region with a large or a highest change, and/or one or more regions to be compared with one or more thresholds; and/or (iv) detect a pre-blood clearance state existing before blood is cleared or partially cleared and/or a post-blood clearance state existing after blood is cleared or partially cleared such that the detection of the pre-blood clearance state and/or the post-blood clearance state is/are used as additional data to calculate or determine the clearance metric more efficiently or accurately as compared to not using the additional data.

6. The imaging device of claim 4, wherein one or more of the following:

(i) where a first frame or frames of the region of interest (ROI) are identified as an original image(s) or frame(s) of the region of interest (ROI), the original image(s) or frame(s) of the region of interest (ROI) are acquired for several frames including one or more of the following: the object, target, or sample being a blood filled lumen; the object, target, or sample being a partially clear lumen; diagnostically clear vessel wall(s) for the object, target, or sample being a vessel; a blood filled object, target, or sample; a partially clear object, target, or sample; and/or a diagnostically clear object, target, or sample;

(ii) the threshold is a pre-determined or set threshold value;

(iii) where a clearance metric is computed or determined, the clearance metric is computed for n segments of the region of interest (ROI), where n is one or more of the following: an integer value from 2 and up to half the number of processed A-lines in the region of interest (ROI), is in the range of 2 to 4, and/or is in the range of 2 to 8;

(iv) the threshold is set so that the automatic pullback is triggered after the partial clearing or only after the diagnostic clearing is achieved;

(v) the threshold is set to optimize the automatic pullback such that time taken from issuance of a trigger pullback to an actual motion of a pullback mechanism is in a tens of milliseconds range; and/or (vi) the threshold is set to a high value such that the clearance metric only exceeds the threshold for an image that is equivalent or substantially equivalent to a diagnostically clear image, or the threshold is set low for a situation where a delay between the issuance of the trigger pullback to the actual motion of the pullback mechanism is larger than 100 milliseconds such that the clearance metric exceeds the low threshold for an image that is equivalent or substantially equivalent to a partly or partially clear image.

7. The imaging device of claim 4, wherein the one or more processors further operate to one or more of the following:

(i) use digitizers or modern digitizers that have one or more built-in Field Programmable Gate Arrays ("FPGAs") for controlling data flow that are capable of OCT processing;

(ii) perform the OCT processing including one or more of the following: windowing of data, zero-padding, Fast Fourier Transform (FFT), magnitude calculation, and/or taking a logarithm of a result before issuance of a trigger pullback signal;

(iii) after an issuance of a trigger pullback signal, transfer raw data from the digitizer or the modern digitizer, and save and process the raw data at a lower rate than a rate at which the raw data was acquired; and/or (iv) use a single channel for faster processing of data before issuance of a trigger pullback signal, and, after the issuance of the trigger pullback signal, use two detection channels.

8. The imaging device of claim 4, wherein the one or more processors further operate to one or more of the following:

(i) keep the clearance metric for more than one frame and use a preliminary threshold for a pre-trigger that is indicative of a partial clearing;

(ii) compare the clearance metric to a pre-trigger threshold, detect that a trigger pullback threshold is reached, and start the trigger pullback where the clearance metric has exceeded the pre-trigger threshold for a set or predetermined minimum number of frames;

(iii) compare a pre-trigger threshold to the clearance metric for a set or predetermined minimum number of frames, the set or predetermined minimum number of frames is-being one or more; and/or (iv) compare the clearance metric to the threshold where the threshold is a trigger pullback threshold, and issue the signal to trigger the pullback where one or more frames have the clearance metric exceed the trigger pullback threshold.

9. A method for triggering an automatic pullback, the method comprising:

collecting image data from an object, target, or sample, and obtaining or identifying a reference frame for a region of interest (ROI) in the image data;

determining an amount of a change in an image intensity of each of one or more other frames of the image data showing the region of interest (ROI) relative to an image intensity of the region of interest (ROI) shown or as in the reference frame;

determining whether the amount of, or a level in, the change for each of the one or more other frames of the image data showing the region of interest (ROI) indicates that a partial clearing or a diagnostic clearing of the object, target, or sample is or has been achieved where a clearance metric is above a threshold; and issuing a signal based on the determined amount of, or the determined level in, the change indicating that the partial clearing or the diagnostic clearing of the object, target, or sample is or has been achieved and based on the clearance metric being above the threshold, the signal operating to be used to trigger the automatic pullback.

10. The method of claim 9, further comprising one or more of the following:

(i) acquiring a next frame of the region of interest (ROI);

(ii) isolating the region of interest (ROI) such that in a pre-scan conversion domain data is selected such that a band of two-dimensional (2D) images start a few pixels outside an outer radius of a catheter and extend for a depth equivalent to about a light penetration depth in blood;

(iii) receiving one or more imaging modality frames at a rate of up to 200 frames per second;

(iv) selecting the region of interest (ROI) from about 90 pixels in depth to 160 pixels in depth and for either all A-lines of an image or frame or from A-line 1 to A-line 500 of the image or frame;

(v) capturing the reference frame in a low rotation speed mode for a catheter of the imaging device and/or for the imaging device and adjusting the reference frame to match the ROI region of interest (ROI) for frames used to detect the automatic pullback trigger;

(vi) capturing the reference frame in a low rotation speed mode for a catheter of the imaging device and/or for the imaging device and adjusting the reference frame to match the region of interest (ROI) for frames used to detect the automatic pullback trigger, and using the region of interest (ROI) shown or as in the reference frame as a reference region of interest (ROI), instead of acquiring the next frame region of interest (ROI), values from the reference frame being indicative of or show a possible preclearing image; and/or (vii) determining whether a possible preclearing image includes a case where contrast is or was administered by mistake before an imaging device was put in a pre-record mode and/or a pullback mode.

11. The method of claim 9, further comprising one or more of the following:

(i) processing or displaying the region of interest (ROI) as an annulus on a scan converted image of the object, target, or sample being a partly cleared vessel image with overlaid annulus inner and outer rings;

(ii) processing or displaying the region of interest (ROI) with a blacked out background for the image beyond an annulus;

(iii) performing subsampling in the A-lines direction to improve or optimize processing; and/or (iv) processing the subsampling every other A-line or one A-line for every three or more A-lines.

12. The method of claim 9, further comprising one or more of the following:

(i) acquiring a next frame of the region of interest (ROI), or using the region of interest (ROI) shown or as in the reference frame as a reference region of interest (ROI) and having values from the reference frame being indicative of a possible preclearing image;

(ii) identifying a first frame of the region of interest (ROI);

(iii) storing the first frame as an original image of the region of interest (ROI);

(iv) storing the first frame as an original image of the region of interest (ROI) in a memory;

(v) computing or determining the clearance metric, the clearance metric including a comparison of data, or intensity value(s), for one or more frames of the region of interest (ROI) with data, or intensity value(s), for the reference frame, or the clearance metric operating to measure the amount of, or the level in, the change; and/or (vi) determining that the clearance metric is not above the threshold, then returning to acquire a next frame of the region of interest (ROI), and computing or determining a new clearance metric until the clearance metric is above the threshold.

13. The method of claim 12, further comprising one or more of the following:

(i) subtracting every subsequent frame region of interest (ROI) data from the reference region of interest (ROI), the region of interest (ROI) shown or as in the reference frame being used as a reference region of interest (ROI) and values from the reference frame being indicative of a possible preclearing image;

(ii) subtracting every subsequent frame region of interest (ROI) data from the reference region of interest (ROI) such that substantially similar features or the same features are substantially subtracted or are subtracted from each other, the region of interest (ROI) shown or as in the reference frame being used as a reference region of interest (ROI) and values from the reference frame being indicative of a possible preclearing image;

(iii) calculating or determining the clearance metric to be one or more of the following: a sum or mean value for 8-bit unsigned integer values in the region of interest (ROI) of all subsequent frames, a sum or mean value for 8-bit unsigned integer intensity values in region of interest (ROI) data of all subsequent frames subtracted from a reference region of interest (ROI) the region of interest (ROI) shown or as in the reference frame being used as the reference region of interest (ROI) and values from the reference frame being indicative of a possible preclearing image such that the subtraction produces a resultant signal, a sum or mean value for 8-bit unsigned integer intensity values in region of interest (ROI) data of all subsequent frames subtracted from a reference region of interest (ROI) then divided by a mean of a current frame region of interest (ROI) in the region of interest (ROI) shown or as in the reference frame is being used as the reference region of interest (ROI) and values from the reference frame being indicative of a possible preclearing image such that the subtraction produces a resultant signal, a sum or mean value for 8-bit unsigned integer intensity values in region of interest (ROI) data of all subsequent frames subtracted from a reference region of interest (ROI) then divided by a mean of the reference ROI-region of interest (ROI) region of interest (ROI) shown or as in the reference frame being used as the reference region of interest (ROI) and values from the reference frame being indicative of a possible preclearing image such that the subtraction produces a resultant signal, a mean region of interest (ROI) value of a resultant signal generated by subtracting region of interest (ROI) data of one or more frames from a reference region of interest (ROI), a mean region of interest (ROI) value of a resultant signal relative to a mean region of interest (ROI) value from the region of interest (ROI) shown or as in the reference frame, a mean region of interest (ROI) value of a resultant signal generated by subtracting region of interest (ROI) data of one or more frames from a reference frame relative to a mean region of interest (ROI) value from a region of interest (ROI) value of a current frame, a region with a large or a highest change, and/or one or more regions to be compared with one or more thresholds; and/or (iv) detecting a pre-blood clearance state existing before blood is cleared or partially cleared and/or a post-blood clearance state existing after blood is cleared or partially cleared such that the detection of the pre-blood clearance state and/or the detection of the post-blood clearance state is/are used as additional data to calculate or determine the clearance metric more efficiently or accurately as compared to not using the additional data.

14. A non-transitory computer-readable storage medium storing a computer-readable program for causing a computer to execute a method for triggering an automatic pullback, the method comprising:

collecting image data from an object, target, or sample, and obtaining or identifying a reference frame for a region of interest (ROI) in the image data;

determining an amount of a change in an image intensity of each of one or more other frames of the image data showing the region of interest (ROI) relative to an image intensity of the region of interest (ROI) shown or as in the reference frame;

determining whether the amount of, or a level in, the change for each of the one or more other frames of the image data showing the of interest (ROI) indicates that a partial clearing or a diagnostic clearing of the object, target, or sample is or has been achieved where a clearance metric is above a threshold; and issuing a signal based on the determined amount of, or the determined level in, the change indicating that the partial clearing or the diagnostic clearing of the object, target, or sample is or has been achieved and based on the clearance metric being above the threshold, the signal operating to trigger the automatic pullback.

* * * * *